(12) United States Patent
Park

(10) Patent No.: US 11,183,614 B2
(45) Date of Patent: Nov. 23, 2021

(54) SEMICONDUCTOR DEVICE

(71) Applicant: SUZHOU LEKIN SEMICONDUCTOR CO., LTD., Taicang (CN)

(72) Inventor: Su Ik Park, Seoul (KR)

(73) Assignee: SUZHOU LEKIN SEMICONDUCTOR CO., LTD., Taicang (CN)

( * ) Notice: Subject to any disclaimer, the term of this patent is extended or adjusted under 35 U.S.C. 154(b) by 492 days.

(21) Appl. No.: 16/319,051

(22) PCT Filed: Jul. 20, 2017

(86) PCT No.: PCT/KR2017/007830
§ 371 (c)(1),
(2) Date: Jan. 18, 2019

(87) PCT Pub. No.: WO2018/016894
PCT Pub. Date: Jan. 25, 2018

(65) Prior Publication Data
US 2021/0305461 A1    Sep. 30, 2021

(30) Foreign Application Priority Data

Jul. 20, 2016  (KR) .......................... 10-2016-0092306
Jul. 27, 2016  (KR) .......................... 10-2016-0095706

(51) Int. Cl.
*H01L 33/46*  (2010.01)
*H01L 33/22*  (2010.01)
(Continued)

(52) U.S. Cl.
CPC ............... *H01L 33/46* (2013.01); *A61L 2/10* (2013.01); *A61L 2/26* (2013.01); *H01L 33/22* (2013.01);
(Continued)

(58) Field of Classification Search
CPC ......... H01L 33/10; H01L 33/32; H01L 33/06; H01L 33/405; H01L 33/22
See application file for complete search history.

(56) References Cited

U.S. PATENT DOCUMENTS 9,159,879 B2 * 10/2015 Matsumura ............. H01L 33/44
2005/0056855 A1     3/2005 Lin et al.
(Continued)

FOREIGN PATENT DOCUMENTS

CN    102906888 A    1/2013
CN    103390713 A    11/2013
(Continued)

OTHER PUBLICATIONS

International Search Report dated Oct. 27, 2017 issued in Application No. PCT/KR2017/007830.
(Continued)

*Primary Examiner* — Dung A. Le
(74) *Attorney, Agent, or Firm* — Birch, Stewart, Kolasch & Birch, LLP

(57) ABSTRACT

One embodiment discloses a semiconductor device comprising: a semiconductor structure, which comprises a first conductive semiconductor layer, a second conductive semiconductor layer, and an active layer arranged between the first conductive semiconductor layer and the second conductive semiconductor layer, and comprises a plurality of first recesses arranged up to a partial area of the first conductive semiconductor layer by penetrating the second conductive semiconductor layer and the active layer, and a second recess arranged between the plurality of first recesses; a plurality of first electrodes arranged inside the plurality of first recesses, and electrically connected with the first conductive semiconductor layer; a plurality of second electrodes electrically connected to the second conductive semiconductor layer; and a reflective layer arranged inside
(Continued)

the second recess, wherein the sum of the area of the plurality of first recesses and the area of the second recess is 60% or less of the maximum area in a first direction of the semiconductor structure, the area of the plurality of first recesses and the area of the second recess are the areas formed on the lower surface of the semiconductor structure, and the first direction is vertical to the thickness direction of the semiconductor structure.

18 Claims, 33 Drawing Sheets

(51) Int. Cl.
    *A61L 2/10*        (2006.01)
    *A61L 2/26*        (2006.01)
    *H01L 33/38*     (2010.01)

(52) U.S. Cl.
    CPC ......... *H01L 33/382* (2013.01); *A61L 2202/11* (2013.01)

(56) References Cited

U.S. PATENT DOCUMENTS

| | | |
|---|---|---|
| 2007/0176188 A1 | 8/2007 | Tanaka et al. |
| 2010/0078656 A1* | 4/2010 | Seo .................... H01L 25/0753 257/88 |
| 2013/0334552 A1 | 12/2013 | Yang et al. |
| 2015/0140702 A1 | 5/2015 | Ikeda |
| 2016/0064617 A1 | 3/2016 | Yang et al. |
| 2016/0093769 A1 | 3/2016 | vom Dorp et al. |
| 2018/0219133 A1* | 8/2018 | Park ........................ H01L 33/46 |
| 2019/0127504 A1* | 5/2019 | Okada ............... C08F 216/1416 |

FOREIGN PATENT DOCUMENTS

| | | |
|---|---|---|
| DE | 10 2008 034708 | 2/2010 |
| JP | 2005-093970 | 4/2005 |
| JP | 2008-205005 A | 9/2008 |
| JP | 2011-29612 A | 2/2011 |
| JP | 2012-195321 A | 10/2012 |
| JP | 2015-103536 | 6/2015 |
| JP | 2015-173294 | 10/2015 |
| JP | 2016-66691 A | 4/2016 |
| KR | 10-2011-0117964 | 10/2011 |
| KR | 10-2012-0067782 | 6/2012 |
| KR | 10-2013-0139630 | 12/2013 |
| KR | 10-2016-0024370 A | 3/2016 |
| WO | WO 2015/025631 A1 | 2/2015 |
| WO | WO 2017/034356 | 3/2017 |

OTHER PUBLICATIONS

European Search Report dated Feb. 6, 2020 issued in Application No. 17831367.2.

* cited by examiner

SEMICONDUCTOR DEVICE

CROSS-REFERENCE TO RELATED PATENT APPLICATIONS

This application is a U.S. National Stage Application under 35 U.S.C. § 371 of PCT Application No. PCT/KR2017/007830, filed Jul. 20, 2017, which claims priority to Korean Patent Application No's. 10-2016-0092306, filed Jul. 20, 2016 and 10-2016-0095706, filed Jul. 27, 2016, whose entire disclosures are hereby incorporated by reference.

TECHNICAL FIELD

Embodiments relate to a semiconductor device.

BACKGROUND ART

Semiconductor devices including compounds, such as GaN, AlGaN, and the like, have many advantages such as wide and easily adjustable bandgap energy and the like, and can be variously used as light emitting devices, light receiving devices, various diodes, and the like.

Specifically, a light emitting device such as a light emitting diode or a laser diode using a Group III-V or II-VI compound semiconductor material may realize various colors, such as red light, green light, blue light, ultraviolet light, and the like, resulting from development of a thin film growth technique and a device material, and white light with high efficiency using a phosphor or by combining colors, and has advantages of low power consumption, a semi-permanent lifetime, a fast response time, safety, and environment friendliness when compared to conventional light sources such as fluorescent lamps and incandescent lamps.

In addition, when a light receiving device such as a photodetector or a solar cell is manufactured using a Group III-V or II-VI compound semiconductor material, due to development of an element material, the light receiving device absorbs light of various wavelength regions to generate a photoelectric current so that light in various wavelength regions from gamma rays to a radio wavelength region may be used. Further, with advantages of a fast response speed, safety, environmental friendliness, and easy control of a device material, the light receiving device can also be easily used for power control, a microwave circuit, or a communication module.

Accordingly, application of the semiconductor device has expanded to a transmission module of an optical communication device, a light emitting diode (LED) backlight replacing a cold cathode fluorescent lamp (CCFL) that configures a backlight of a liquid crystal display (LCD) device, a white LED lighting device capable of replacing a fluorescent lamp or an incandescent lamp, a headlight of a vehicle, traffic lights, a sensor for detecting a gas or fire, and the like. Further, the application of the semiconductor device can be expanded to a high frequency application circuit, other power control device, and a communication module.

Particularly, a light-emitting device emitting light in an ultraviolet wavelength range can be used for curing, a medical use, and sterilization by acting curing and sterilization.

In a conventional semiconductor device, light generated in an active layer can propagate to a lateral surface or in a downward direction of the active layer in addition to an upward direction thereof. In particular, as an aluminum (Al) composition increases, a quantity of light emitted to the lateral surface can be increased. Therefore, there is a problem in that a propagation path of the light emitted from the semiconductor device becomes longer or the light is absorbed inside a semiconductor structure.

DISCLOSURE

Technical Problem

Exemplary embodiments are directed to providing a semiconductor device with improved extraction efficiency of light.

Further, exemplary embodiments are directed to providing a semiconductor device with improved optical power and a reduced operating voltage.

Technical Solution

One aspect of the present invention provides a semiconductor device including a semiconductor structure having a first conductive semiconductor layer, a second conductive semiconductor layer, an active layer disposed between the first conductive semiconductor layer and the second conductive semiconductor layer, a plurality of first recesses disposed up to some region of the first conductive semiconductor layer by passing through the second conductive semiconductor layer and the active layer, and a second recess disposed between the plurality of first recesses; a plurality of first electrodes disposed inside the plurality of first recesses and electrically connected to the first conductive semiconductor layer; a plurality of second electrodes electrically connected to the second conductive semiconductor layer; and a reflective layer disposed inside the second recess, wherein the sum of areas of the plurality of first recesses and an area of the second recess may be in the range of 60% or less relative to a maximum area of the semiconductor structure in a first direction, the areas of the plurality of first recesses and the area of the second recess may be areas formed on a lower surface of the semiconductor structure, and the first direction may be a direction perpendicular to a thickness direction of the semiconductor structure.

A distance between the plurality of second electrodes may be in the range of 3 μm to 60 μm.

A width of the reflective layer may be in the range of 3 μm to 30 μm.

The distance between the plurality of second electrodes may be equal to the width of the reflective layer.

An area in which the plurality of first electrodes are electrically connected to the first conductive semiconductor layer may be in the range of 6.0% to 11.0% relative to the maximum area of the semiconductor structure in the first direction.

An area in which the plurality of second electrodes are electrically connected to the second conductive semiconductor layer may be in the range of 40% to 60% relative to the maximum area of the semiconductor structure in the first direction.

A ratio of the area in which the plurality of first electrodes are electrically connected to the first conductive semiconductor layer to the area in which the plurality of second electrodes are electrically connected to the second conductive semiconductor layer may be in the range of 1:4 to 1:10.

The semiconductor structure may include a plurality of first regions separated by the second recess, and the plurality of first electrodes may be disposed in the plurality of first regions.

An area of the first region may be 2.0 to 5.0 times an area of the first electrode.

Areas of the plurality of first regions may be 2.0 to 5.0 times the areas of the plurality of first recesses.

The reflective layer may include an extension part extending from the second recess and configured to be in contact with the second electrode.

The reflective layer may include a capping layer configured to cover the reflective layer and the second electrode.

The reflective layer may include a second electrode pad electrically connected to the capping layer.

The semiconductor device may further include a lower reflective layer electrically connected to the plurality of first electrodes.

The semiconductor device may further include a substrate electrically connected to the lower reflective layer.

The semiconductor structure may generate light in an ultraviolet wavelength range.

The first conductive semiconductor layer may include a first layer disposed adjacent to the active layer and a second layer disposed on the first layer, the second layer may have an aluminum (Al) composition that is higher than that of the first layer, and the first electrode may be disposed on the first layer.

Another aspect of the present invention provides a semiconductor device including a semiconductor structure having a first conductive semiconductor layer, a second conductive semiconductor layer, an active layer disposed between the first conductive semiconductor layer and the second conductive semiconductor layer, a plurality of first recesses disposed up to some region of the first conductive semiconductor layer by passing through the second conductive semiconductor layer and the active layer, and a second recess disposed between the plurality of first recesses; a plurality of first electrodes disposed inside the plurality of first recesses and electrically connected to the first conductive semiconductor layer; a plurality of second electrodes electrically connected to the second conductive semiconductor layer; and a reflective layer disposed inside the second recess, wherein the semiconductor structure may include a plurality of first regions separated by the second recess, and an area ratio of the first recess to the first region may be in the range of 1:4 to 1:8.

The plurality of second electrodes may include a plurality of sub-electrodes disposed in the first region.

The semiconductor structure may include a second region disposed between a lateral surface of the semiconductor structure and the second recess.

A separation distance between the second recess and the lateral surface of the semiconductor structure may be in the range of 1.0 μm to 10 μm.

The plurality of second electrodes may include an edge electrode disposed in the second region.

Advantageous Effects

In accordance with the exemplary embodiments, extraction efficiency of light can be improved.

Further, in accordance with the exemplary embodiments, optical power can be improved.

Furthermore, in accordance with the exemplary embodiments, an operating voltage can be improved.

Various beneficial advantages and effects of the present invention are not limited by the detailed description and should be easily understood through a description of a detailed embodiment of the present invention.

MODES OF THE INVENTION

Exemplary embodiments may be modified in other forms or various embodiments may be combined with each other, and the scope of the present invention is not limited to each embodiment described below.

Although an item described in a specific embodiment is not described in other embodiment, unless otherwise described in the other embodiment or as long as there is no contradictory description therein, the item may be understood as being related to the other embodiment.

For example, when a feature for a configuration A is described in a specific embodiment and a feature for a configuration B is described in other embodiment, even when an embodiment in which the configuration A and the configuration B are combined is not explicitly described, unless otherwise described in the other embodiment or as long as there is no contradictory explanation therein, it should be understood that the combined embodiment will fall within the scope of the present invention.

In the description of the embodiments, when an element is described as being formed "on" or "under" another element, the terms "on" or "under" includes the meaning of the two elements bring in direct contact with each other (directly) and the meaning of one or more other elements being disposed and formed between the two elements (indirectly). Further, when an element is described as being formed "on" or "under" another element, the description may include the meaning of the other element being formed in an upward direction of the element and formed in a downward direction of the element.

Hereinafter, exemplary embodiments of the present invention will be fully described in detail which are suitable for implementation by those skilled in the art to which the present invention pertains with reference to the accompanying drawings.

Figure 1:
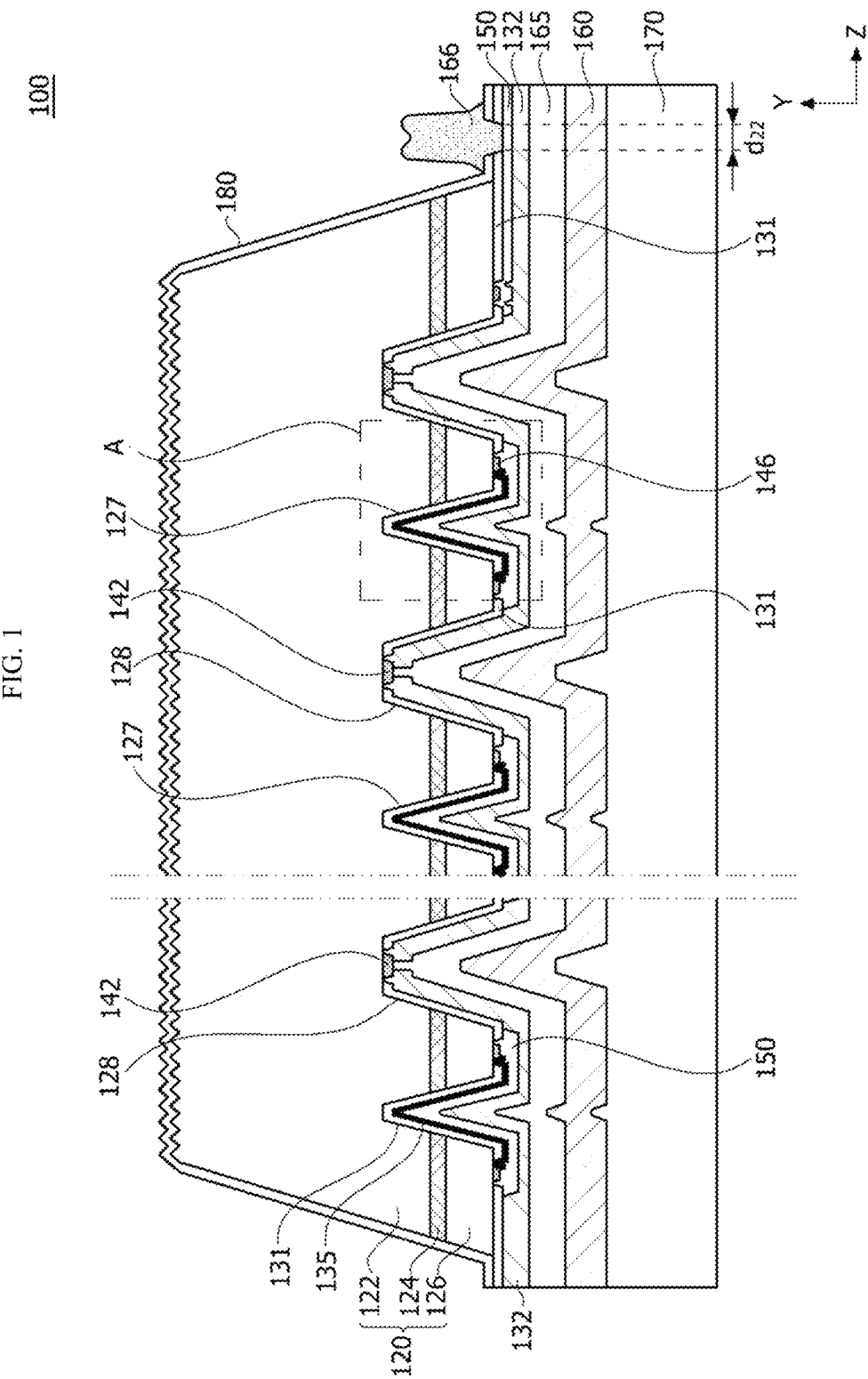
FIG. 1 is a cross-sectional view illustrating a semiconductor device according to an embodiment.
Figure 2:
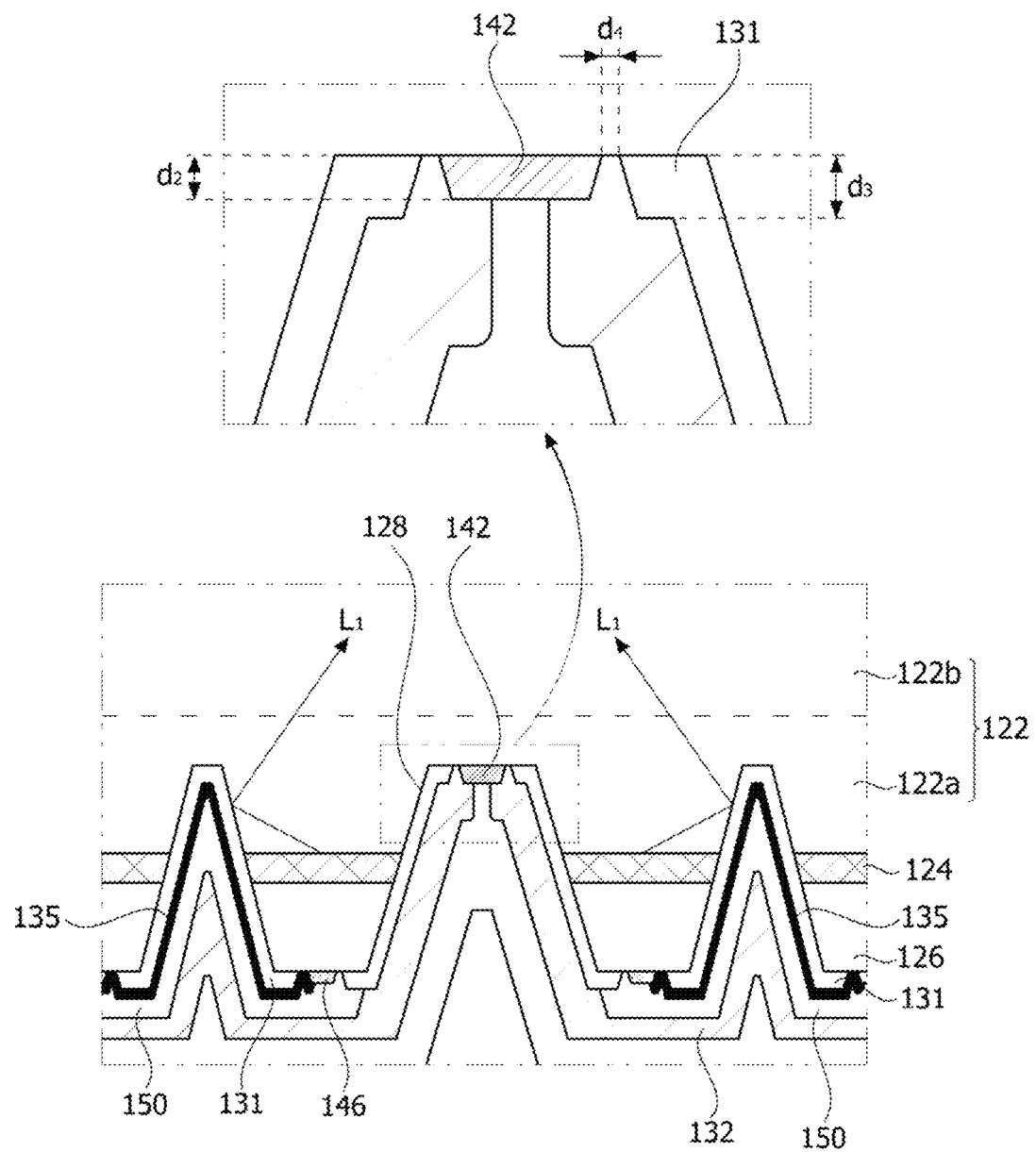
FIG. 2 is a conceptual diagram illustrating a process in which light is reflected upward by a reflective layer.
Figure 3:
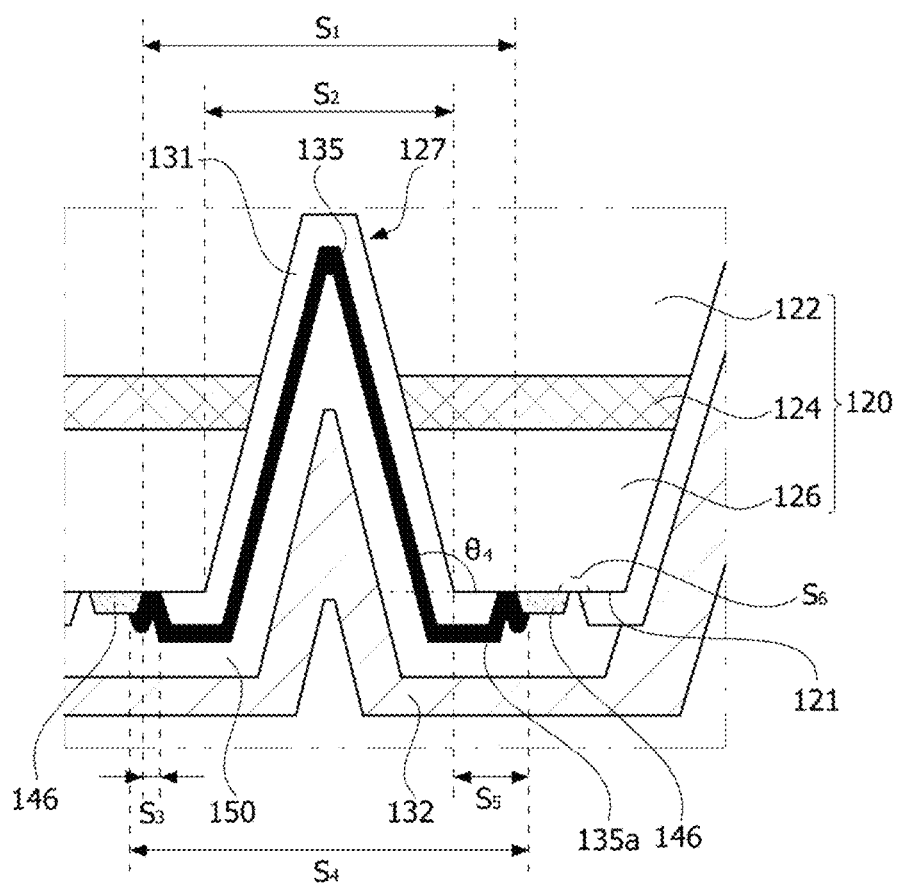
FIG. 3 is an enlarged view of Portion A of FIG. 1.
Figure 4:
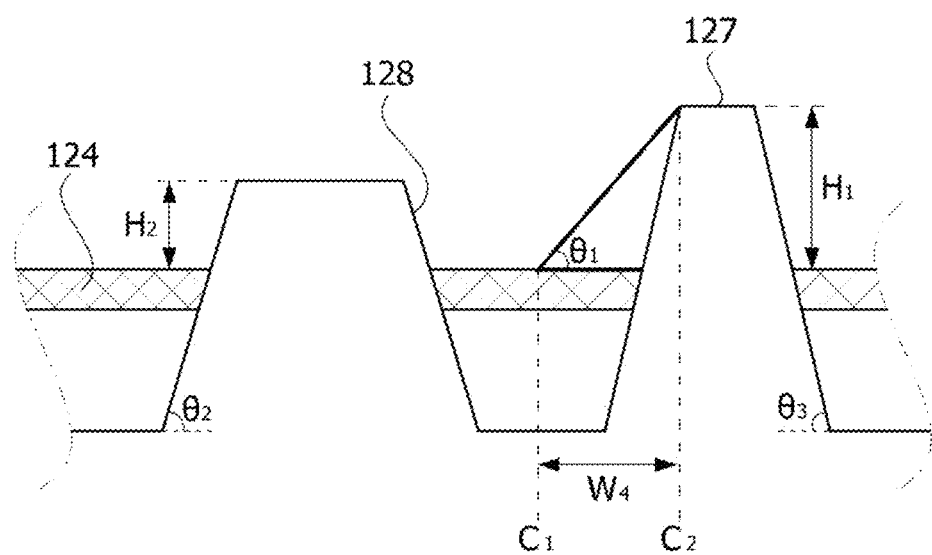
FIG. 4 is a diagram for describing a difference in height between a first recess and a second recess.

FIG. 1 is a cross-sectional view illustrating a semiconductor device according to one embodiment of the present invention, FIG. 2 is a conceptual diagram illustrating a process in which light is reflected upward by a reflective layer, FIG. 3 is an enlarged view of Portion A of FIG. 1, and FIG. 4 is a diagram for describing a difference in height between a first recess and a second recess.

Referring to FIG. 1, the semiconductor device according to the present embodiment includes a semiconductor structure 120 having a first conductive semiconductor layer 122, a second conductive semiconductor layer 126, and an active layer 124, a first electrode 142 electrically connected to the first conductive semiconductor layer 122, a second electrode 146 electrically connected to the second conductive semiconductor layer 126, and a reflective layer 135 disposed in a second recess 127.

The semiconductor structure 120 according to the present embodiment may output light in an ultraviolet (UV) wavelength range. For example, the semiconductor structure 120 may emit light in a near-UV wavelength range (UV-A), light in a far-UV wavelength range (UV-B), or light in a deep-UV wavelength range (UV-C). The UV wavelength range may be determined by an aluminum (Al) composition ratio of the semiconductor structure 120.

For example, the UV-A light in the near-UV wavelength range may have a wavelength in the range of 320 nm to 420 nm, the UV-B light in the far-UV wavelength range may have a wavelength in the range of 280 nm to 320 nm, and the UV-C light in the deep-UV wavelength range may have a wavelength in the range of 100 nm to 280 nm.

When the semiconductor structure 120 emits light in the UV wavelength range, each of the semiconductor layers of the semiconductor structure 120 may include a material of $In_{x1}Al_{y1}Ga_{1-x1-y1}N$ ($0 \leq x1 \leq 1$, $0 < y1 \leq 1$, and $0 \leq x1+y1 \leq 1$) containing Al. Here, an Al composition may be represented by a ratio of a total atomic weight including an In atomic weight, a Ga atomic weight, and an Al atomic weight to the Al atomic weight. For example, when the Al composition is 40%, a 60% Ga composition may be represented as $Al_{40}Ga_{60}N$.

Further, in the description of the present embodiment, the meaning that a composition is low or high can be understood as a difference (a percent (%) point) in composition % between the semiconductor layers. For example, when an Al composition of a first semiconductor layer is 30% and an Al composition of a second semiconductor layer is 60%, it can be expressed that the Al composition of the second semiconductor layer is 30% higher than the Al composition of the first semiconductor layer.

The semiconductor structure 120 includes a plurality of first recesses 128 formed to some region of the first conductive semiconductor layer 122 by passing through the second conductive semiconductor layer 126 and the active layer 124, and at least one second recess 127 disposed between the plurality of first recesses 128.

A first insulating layer 131 may be formed on the first recess 128 and the second recess 127. The first insulating layer 131 may electrically insulate the reflective layer 135 from the active layer 124 and the first conductive semiconductor layer 122. The first insulating layer 131 may extend from the first recess 128 and the second recess 127 to the second conductive semiconductor layer 126.

The first electrode 142 and the second electrode 146 may be ohmic electrodes. Each of the first electrode 142 and the second electrode 146 may be formed of at least one among an indium tin oxide (ITO), an indium zinc oxide (IZO), an indium zinc tin oxide (IZTO), an indium aluminum zinc oxide (IAZO), an indium gallium zinc oxide (IGZO), an indium gallium tin oxide (IGTO), an aluminum zinc oxide (AZO), an antimony tin oxide (ATO), a gallium zinc oxide (GZO), an IZO nitride (IZON), Al—Ga ZnO (AGZO), an IGZO, ZnO, IrOx, RuOx, NiO, RuOx/ITO, Ni/IrOx/Au, Ni/IrOx/Au/ITO, Ag, Ni, Cr, Ti, Al, Rh, Pd, Ir, Sn, In, Ru, Mg, Zn, Pt, Au, and Hf, but the present invention is not limited to these materials.

The reflective layer 135 may be disposed inside the second recess 127. In particular, the reflective layer 135 may be disposed on the first insulating layer 131 in the second recess 127.

The reflective layer 135 may be formed of a material having high reflectance in the UV wavelength range. The reflective layer 135 may include a conductive material. For example, the reflective layer 135 may include Al. When a thickness of the Al reflective layer 135 is in the range of about 30 nm to 100 nm, light in the UV wavelength range may be reflected by 80% or more. Accordingly, it is possible to prevent light emitted from the active layer 124 from being absorbed in the semiconductor layer.

Referring to FIG. 2, when the Al composition of the semiconductor structure 120 increases, a current distribution characteristic in the semiconductor structure 120 may be degraded. Further, the active layer 124 increases a quantity of light emitted to a lateral surface thereof (a transverse magnetic (TM) mode) when compared to a GaN-based blue light emitting device. This TM mode may occur in the UV semiconductor device.

According to the present embodiment, a portion of a region in which a current density is low is etched to form the reflective layer 135 such that light L1 may be reflected upward by the reflective layer 135. Consequently, it is possible to reduce light absorption in the semiconductor structure 120 and improve extraction efficiency of the light. Further, directivity of the semiconductor device may be adjusted.

The first conductive semiconductor layer 122 may be formed of a Group III-V or II-VI compound semiconductor and may be doped with a first dopant. The first conductive semiconductor layer 122 may be formed of a semiconductor material having a composition formula of $In_{x1}Al_{y1}Ga_{1-x1-y1}N$ ($0 \le x1 \le 1$, $0 \le y1 \le 1$, and $0 \le x1+y1 \le 1$) and selected from among, e.g., AlGaN, AlN, InAlGaN, and the like. Further, the first dopant may be an n-type dopant such as Si, Ge, Sn, Se, or Te. When the first dopant is an n-type dopant, the first conductive semiconductor layer 122 doped with the first dopant may be an n-type semiconductor layer.

The first conductive semiconductor layer 122 may have a first layer 122a having a relatively low Al composition and a second layer 122b having a relatively high Al composition. The second layer 122b may have the Al composition in the range of 60% to 70%, and the first layer 122a may have the Al composition in the range of 40% to 50%. The first layer 122a may be disposed adjacent to the active layer 124. The Al composition of the first layer 122a may be higher than that of a well layer. In this case, the first layer 122a may solve a problem in that light generated in the active layer 124 is absorbed. For example, the first layer 122a may have the Al composition that is higher by the range of 5% to 10% than the Al composition of the well layer, but the present invention is not necessarily limited thereto.

The first electrode 142 may be disposed on the first layer 122a to secure a relatively smooth current injection characteristic. That is, the first recess 128 may be preferably formed to a region of the first layer 122a. This is because the second layer 122b has a high Al composition so that a current distribution characteristic of the second layer 122b is relatively low.

The active layer 124 is a layer at which electrons (or holes) injected through the first conductive semiconductor layer 122 and holes (or electrons) injected through the second conductive semiconductor layer 126 meet. The active layer 124 may transition to being a low energy level due to the recombination of electrons and holes and emit light having a wavelength corresponding to the transition.

The active layer 124 may have any one of a single well structure, a multi-well structure, a single quantum well structure, a multi quantum well (MQW) structure in which a well layer and a barrier layer are alternatively disposed, a quantum dot structure, and a quantum wire structure, but the structure of the active layer 124 is not limited thereto. Both the well layer and the barrier layer of the active layer 124 may include Al.

The second conductive semiconductor layer 126 may be formed on the active layer 124, may be formed of a Group III-V or II-VI compound semiconductor, and may be doped with a second dopant. The second conductive semiconductor layer 126 may be formed of a semiconductor material having a composition formula of $In_{x5}Al_{y2}Ga_{1-x5-y2}N$ ($0 \le x5 \le 1$, $0 \le y2 \le 1$, and $0 \le x5+y2 \le 1$) or a material selected from among AlInN, AlGaAs, GaP, GaAs, GaAsP, and AlGaInP. When the second dopant is a p-type dopant such as Mg, Zn, Ca, Sr, or Ba, the second conductive semiconductor layer 126 doped with the second dopant may be a p-type semiconductor layer.

When the second conductive semiconductor layer 126 is made of AlGaN, hole injection may not be smooth due to low electrical conductivity. Therefore, GaN having relatively high electrical conductivity may be disposed at a lower surface the second conductive semiconductor layer 126.

A thickness d2 of the first electrode 142 may be thinner than a thickness d3 of the first insulating layer 131, and a separation distance d4 between the first electrode 142 and the first insulating layer 131 may be provided in the range of 1 μm to 4 μm. The thickness d2 of the first electrode 142 may be 40% to 80% relative to the thickness d3 of the first insulating layer 131.

When the thickness d2 of the first electrode 142 is 40% to 80% relative to the thickness d3 of the first insulating layer 131, it is possible to solve problems such as delamination and cracks due to degradation of a step coverage characteristic which occurs when a lower electrode layer 165 is disposed. Further, the separation distance d4 between the first electrode 142 and the first insulating layer 131 is provided such that a gap-fill characteristic of a second insulating layer 132 may be improved.

Referring to FIG. 3, the reflective layer 135 may cover one lateral surface of the second electrode 146 and a portion of a lower surface of the second electrode 146. With this configuration, light incident between the first insulating layer 131 and the second electrode 146 may be reflected upward. However, the reflective layer 135 such as Al may have a relatively poor step coverage and a leakage current may be generated due to a migration characteristic of the reflective layer 135 such that reliability may be degraded. Consequently, it may not be preferable for the reflective layer 135 to completely cover the second electrode 146.

The second electrode 146 may be disposed on a lower surface 121 of the semiconductor structure. A thickness of the second electrode 146 may be 80% or less relative to a thickness of the first insulating layer 131. Consequently, when the reflective layer 135 and a capping layer 150 are disposed, it is possible to solve problems such as cracks or delamination of the reflective layer 135 or the capping layer 150 due to degradation of a step coverage.

A distance S1 between a plurality of second electrodes may be in the range of 3 and 60 When the distance S1 between the plurality of second electrodes is less than 3 μm, a width of the second recess 127 becomes narrower such that it may be difficult to form the reflective layer 135 inside the second recess 127. Further, if the distance exceeds 60 μm, an area of the second electrode 146 is reduced such that an operating voltage may rise and optical power may be lowered due to a problem of removing an effective light emission region.

A width S2 of the reflective layer may be in the range of 3 μm to 30 μm. When the width S2 of the reflective layer is less than 3 it is difficult to form the reflective layer in the second recess 127, whereas when the width S2 exceeds 30 μm, the area of the second electrode 146 is reduced such that the operating voltage rises. Accordingly, the distance S1 between the plurality of second electrodes may be equal to the width S2 of the reflective layer.

The width S2 of the reflective layer 135 may be equal to the width of the second recess 127. Each of a width of the first recess and the width of the second recess 127 may be a maximum width formed on the lower surface 121 of the semiconductor structure.

The reflective layer 135 may include an extension part 135a extending from the second recess 127 toward the second electrode 146. The extension part 135a may electrically connect the second electrodes 146 separated by the second recess 127.

A width S5 of the extension part 135a may be in the range of 0 μm to 20 μm. When the width S5 is greater 20 the second electrode 146 is completely covered such that the step coverage characteristic may be degraded. A width S4 of the reflective layer including the extension part 135a may be in the range of 20 μm to 60 μm.

A first separation distance S3 between the second electrode 146 and the first insulating layer 131 may be provided in the range of 0 μm to 4 μm. When the first separation distance is longer than 4 μm, an area in which the second electrode 146 is disposed becomes narrower such that the operating voltage may rise.

The reflective layer 135 may be disposed within the first separation distance S3 between the second electrode 146 and the first insulating layer 131 and may be in contact with a lateral surface and an upper surface of the first insulating layer 131 and the lateral surface and an upper surface of the second electrode 146 within the first separation distance S3. Further, a region in which the reflective layer 135 is in Schottky contact with the second conductive semiconductor layer 126 may be disposed within the first separation distance S3 to form a Schottky junction such that a current may be easily distributed.

An angle θ4 between an inclined portion of the reflective layer 135 and the lower surface of the second conductive semiconductor layer 126 may be in the range of 90 degrees to 145 degrees. When the inclination angle θ4 is less than 90 degrees, it is difficult to etch the second conductive semiconductor layer 126, whereas when the inclination angle θ4 is greater than 145 degrees, an etched area of the active layer becomes larger such that light emitting efficiency is degraded.

The capping layer 150 may cover the reflective layer 135 and the second electrode 146. Accordingly, a second electrode pad 166, the capping layer 150, the reflective layer 135, and the second electrode 146 may form one electrical channel.

The capping layer 150 may completely surround the reflective layer 135 and the second electrode 146 and may be in contact with the lateral surface and the upper surface of the first insulating layer 131. The capping layer 150 may be formed of a material having high adhesive strength to the first insulating layer 131, formed of at least one material selected from the group consisting of Cr, Al, Ti, Ni, Au, and the like, and an alloy thereof, and formed of a single layer or a plurality of layers.

When the capping layer 150 is in contact with the lateral surface and the upper surface of the first insulating layer 131, thermal and electrical reliability of the reflective layer 135 and the second electrode 146 may be improved. Further, the capping layer 150 may have a function of reflecting the light, which is emitted between the first insulating layer 131 and the second electrode 146, upward.

The capping layer 150 may be disposed within a second separation distance between the first insulating layer 131 and the second electrode 146. The capping layer 150 may be in contact with the lateral surface and the upper surface of the second electrode 146 and the lateral surface and the upper surface of the first insulating layer 131 within the second separation distance. Further, a region in which the capping layer 150 is in Schottky contact with the second conductive semiconductor layer 126 may be disposed within the second separation distance to form a Schottky junction such that a current may be easily distributed.

Referring back to FIG. 1, the lower electrode layer 165 and a bonding layer 160 may be disposed along a lower surface of the semiconductor structure 120 and topography of the first recess 128 and the second recess 127. The lower electrode layer 165 may be formed of a material having high reflectance. For example, the lower electrode layer 165 may include Al. When the lower electrode layer 165 includes Al, the lower electrode layer 165 serves to reflect light, which is emitted in a direction from the active layer 124 toward a substrate 170, upward such that extraction efficiency of the light may be improved.

The second insulating layer 132 electrically insulates the reflective layer 135, the second electrode 146, and the capping layer 150 from the lower electrode layer 165. The lower electrode layer 165 may be electrically connected to the first electrode 142 by passing through the second insulating layer 132.

The thickness of the first insulating layer 131 may be in the range of 40% to 80% relative to a thickness of the second insulating layer 132. When the range of 40% to 80% is satisfied, the thickness of the first insulating layer 131 becomes thinner and an upper surface of reflective layer 135 becomes closer to the first conductive semiconductor layer 122 such that extraction efficiency of the light may be improved.

For example, the thickness of the first insulating layer 131 may be in the range of 3000 Å and 7000 Å. When the thickness of the first insulating layer 131 is thinner than 3000 Å, electrical reliability may be degraded, whereas when the thickness of the first insulating layer 131 is thicker than 7000 Å and the reflective layer 135 and the capping layer 150 are disposed on the upper portion and the lateral surface of the first insulating layer 131, a step coverage characteristic of the reflective layer 135 or the capping layer 150 is not good such that delamination or cracks may be caused. When delamination or cracks are caused, there may occur a problem in that electrical reliability is degraded or extraction efficiency of light is degraded.

The thickness of the second insulating layer 132 may be in the range of 4000 Å and 10000 Å. When the thickness of the second insulating layer 132 is thinner than 4000 Å, electrical reliability may be degraded when a device operates, whereas when the thickness of the second insulating layer 132 is thicker than 10000 Å, reliability may be degraded due to a pressure or thermal stress applied to the device during a process, and a process time may be prolonged such that a unit cost of the device increases. The thicknesses of the first insulating layer 131 and the second insulating layer 132 are not limited thereto.

The bonding layer 160 may include a conductive material. For example, the bonding layer 160 may include a material selected from the group consisting of Au, Sn, In, Al, Si, Ag, Ni, and copper (Cu), or an alloy thereof.

The substrate 170 may be formed of a conductive material. For example, the substrate 170 may include a metal or a semiconductor material. The substrate 170 may be a metal having high electrical conductivity and/or high thermal conductivity. In this case, heat generated during an operation of the semiconductor device may be rapidly dissipated to the outside.

The substrate 170 may include a material selected from the group consisting of Si, molybdenum (Mo), tungsten (W), Cu, and Al, or an alloy thereof.

The second electrode pad 166 may be made of a conductive material. The second electrode pad 166 may have a single-layer or multi-layered structure and may include Ti, Ni, Ag, and Au. For example, the second electrode pad 166 may have a structure of Ti/Ni/Ti/Ni/Ti/Au.

A central portion of the second electrode pad 166 is depressed so that an upper surface of the second electrode pad 166 may have a concave portion and a convex portion. A wire (not shown) may be bonded to the concave portion of the upper surface. Thus, a bonding area may be widened so that the second electrode pad 166 and the wire may be bonded more firmly.

The second electrode pad 166 may serve to reflect light so that extraction efficiency of the light may be improved as the second electrode pad 166 is disposed to be close to the semiconductor structure 120.

A distance between the second electrode pad 166 and the semiconductor structure 120 may be in the range of between 5 μm and 30 μm. When the distance is less than 10 μm, it is difficult to secure a process margin, whereas when the distance is greater than 30 μm, an area in which the second electrode pad 166 is disposed becomes larger in a total area of the semiconductor device such that an area of a light emitting layer 124 may be reduced and a quantity of light may be decreased.

A height of the convex portion of the second electrode pad 166 may be higher than a height of the active layer 124. Accordingly, the second electrode pad 166 may reflect light, which is emitted from the active layer 124 in a horizontal direction of the semiconductor device, upward such that extraction efficiency of the light may be improved and directivity of the light may be controlled.

Irregularities may be formed on an upper surface of the semiconductor structure. The irregularities may improve extraction efficiency of the light emitted from the semiconductor structure 120. An average height of the irregularities may be different according to a UV wavelength. In the case of UV-C light, when heights of the irregularities are in the range of 300 nm to 800 nm and the average height thereof is in the range of 500 nm to 600 nm, extraction efficiency of the light may be improved.

A passivation layer 180 may be disposed on the upper surface and a lateral surface of the semiconductor structure 120. A thickness of the passivation layer 180 may be in the range of 2000 Å and 5000 Å. When the thickness is thinner than 2000 Å, the passivation layer 180 may not be sufficient to protect the semiconductor device from external moisture or foreign materials and thus may degrade electrical and optical reliability of the semiconductor device, whereas when the thickness is thicker than 5000 Å, stress applied to the semiconductor device may become larger to degrade the optical reliability or the process time may be prolonged to increase a unit cost.

Referring to FIG. 4, a protruding height H1 of the second recess 127 may be higher than a protruding height H2 of the first recess 128. Here, the protruding heights may be defined as vertical distances from the active layer 124 to upper surfaces of the first recess 128 and the second recess 127.

In particular, the protruding height H1 of the second recess 127 may satisfy the following relational expression 1.

$$H1 = W4 \times \tan(\theta 1) \quad \text{[Relational Expression 1]}$$

Here, W4 is a distance from an intermediate point C1 between the first recess 128 and the second recess 127, which are adjacent to each other, to an upper surface C2 of the second recess, and θ1 is in the range of 0.5 degrees to 5.0 degrees.

When θ1 is less than 0.5 degrees, a height of the reflective layer becomes relatively lower such that it may be difficult for the reflective layer to perform an effective reflection function. Further, when θ1 exceeds 5.0 degrees, the height of the reflective layer becomes too high such that there is a problem in that an area of the active layer is excessively decreased in proportional to the height of the reflective layer. Furthermore, there is a problem in that a recess process and an insulating process should be managed more accurately.

For example, the distance from the intermediate point C1 to the upper surface C2 of the second recess may be in the range of 20 μm to 40 μm, and θ1 may be 2.3 degrees. The protruding height of the second recess 127 may be in the range of about 300 nm to 800 nm. In this case, light emitted from the active layer 124 in a TM mode may be effectively reflected upward.

The second recess 127 may be formed to be higher than the first recess 128. However, the present invention is not particularly limited thereto, and a height of the first recess 128 may be equal to that of the second recess 127.

An inclined angle θ2 of the first recess 128 may be in the range of 40 degrees to 70 degrees or 60 degrees to 70 degrees, and an inclined angle θ3 of the second recess 127 may be in the range of 40 degrees to 70 degrees or 60 degrees to 70 degrees.

Figure 5:
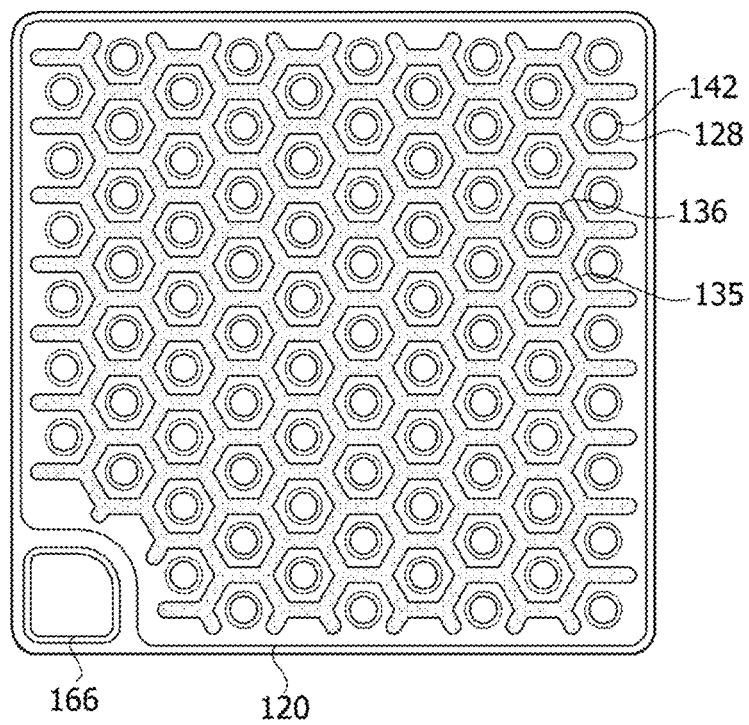
FIG. 5 is a plan view of the semiconductor device according to the embodiment of the present invention.
Figure 6:
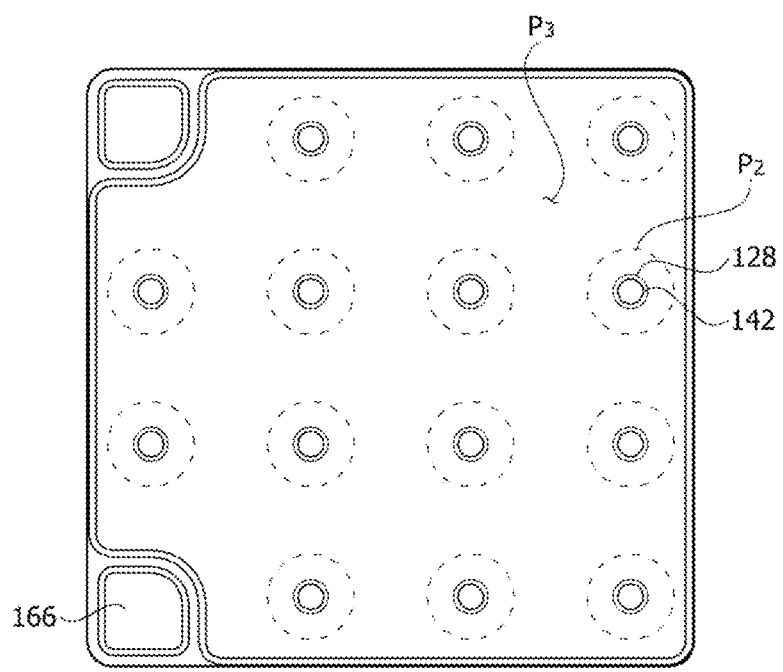
FIG. 6 is a diagram illustrating a distribution of a current density of the semiconductor device.
Figure 7A:
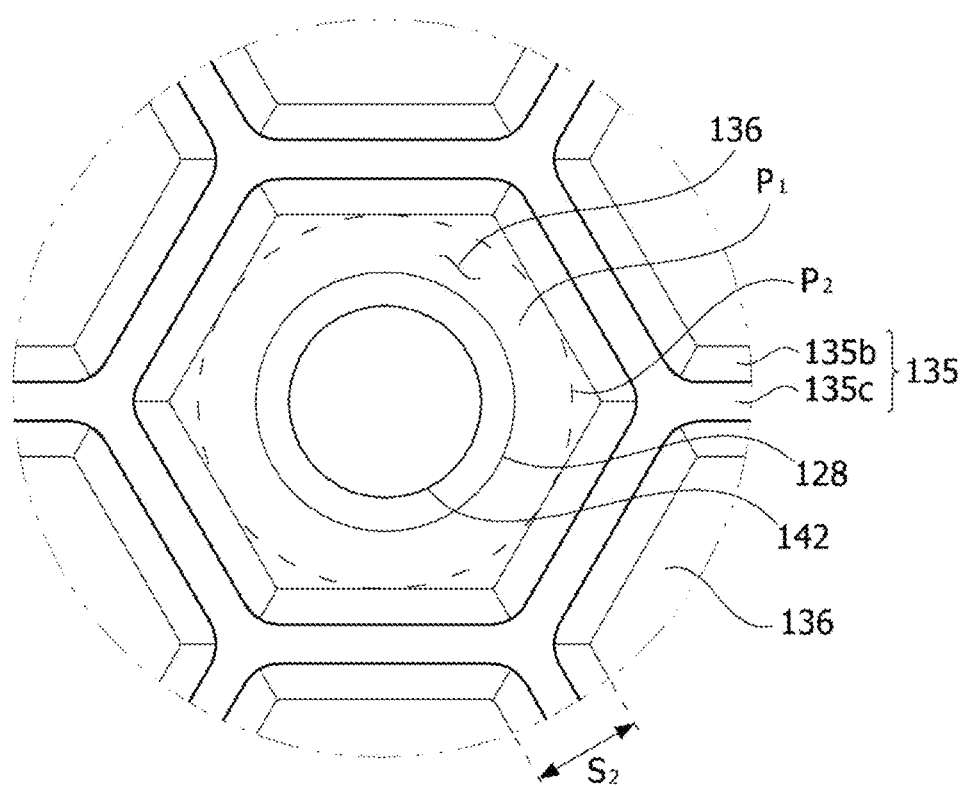
FIG. 7A is a diagram illustrating a first region.
Figure 7B:
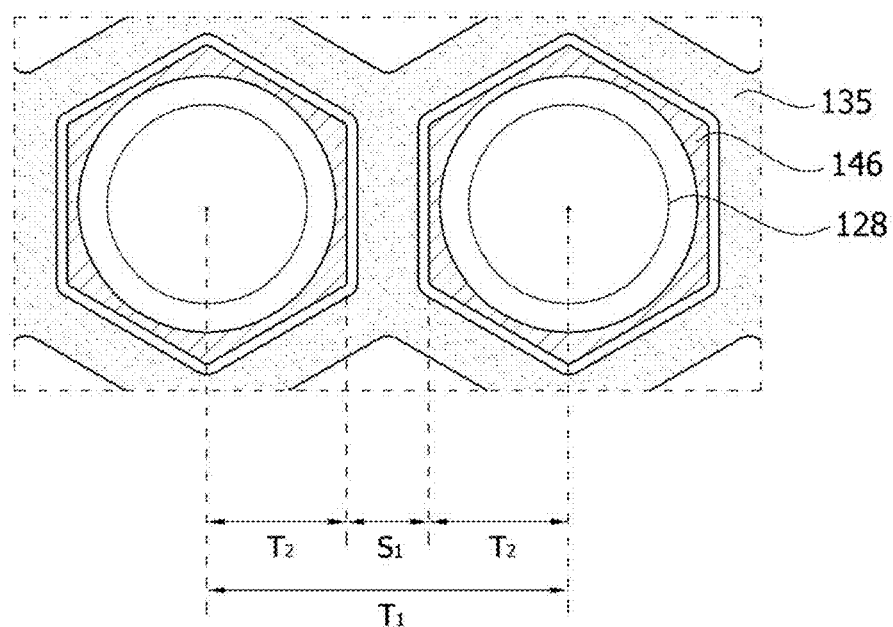
FIG. 7B is a diagram for describing a distance between the first regions.
Figure 8:
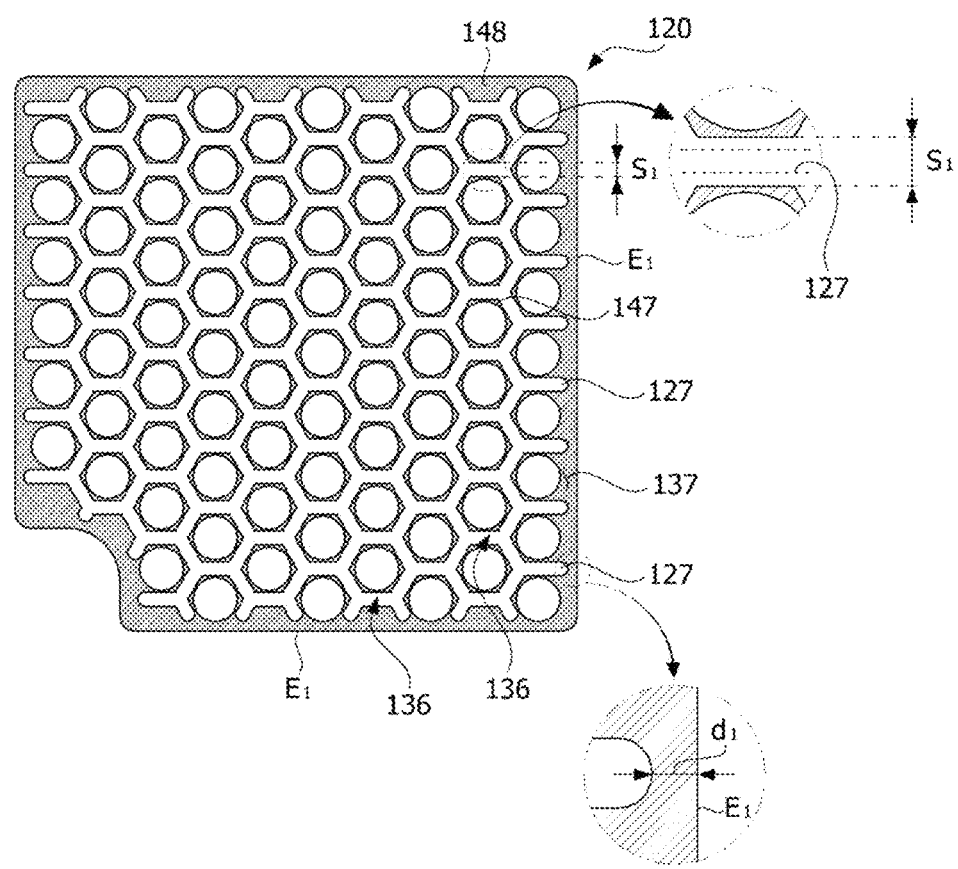
FIG. 8 is a diagram illustrating an area of a p-ohmic electrode.

FIG. 5 is a plan view of the semiconductor device according to the embodiment of the present invention, FIG. 6 is a diagram illustrating a distribution of a current density of the semiconductor device, FIG. 7A is a diagram illustrating a first region, FIG. 7B is a diagram for describing a distance between the first regions, and FIG. 8 is a diagram illustrating an area of a p-ohmic electrode.

Referring to FIG. 5, a semiconductor device 100 may include a plurality of first regions 136, each of which is separated by the reflective layer 135 or the second recess on a plan view. The first recess 128, the second recess, the reflective layer 135, and the first region 136 may be regions formed on the lower surface of the semiconductor structure. The plurality of first regions 136 may be independent spaces separated at predetermined intervals. Further, the plurality of first regions 136 may be light emitting regions.

The first region 136 may have various shapes. For example, the first region 136 may have a polygonal shape, such as a hexagonal, octagonal, or triangular shape, or a circular shape.

Each of a plurality of first electrodes 142 and a plurality of first recess 128 may be disposed in the first region 136. According to such a structure, the reflective layer 135 may surround the first electrode 142 in which a current is distributed. Thus, light emitted in the vicinity of the first electrode 142 may be reflected upward by the reflective layer 135 surrounding the first region 136.

The reflective layer 135 may be disposed in a region in which regions, each of which has a current density of 40% or less relative to a current density of 100% of the first electrode 142, are connected. For example, a distance between a center of the first recess and a center of the second recess disposed on a horizontal line of the first recess may be in the range of 5 μm and 40 μm.

When the distance is shorter than 5 μm, the active layer in a region having high current distribution may be etched to degrade light emission efficiency, whereas when the distance is longer than 40 μm, a region with a poor current distribution characteristic remains such that extraction efficiency of light may be degraded. When the reflective layer is formed in a region having a current density of less than 30%, the light emitting region may excessively become wider such that the extraction efficiency of the light may be degraded. Further, there is a high possibility that a considerable portion of the light emitted to a lateral surface is absorbed in the semiconductor structure.

Referring to FIG. 6, when an Al composition increases, a current distribution effect may be degraded. Accordingly, a current is distributed only in the vicinity of the first electrode 142 such that a current density may be drastically lowered at a position away from the first electrode 142. Therefore, an effective light emitting region P2 becomes narrower.

The effective light emitting region P2 may be defined as a boundary position at which a current density is in the range of 30% to 40% relative to a position P1 in the vicinity of the first electrode, at which the current density is highest. For example, a distance separated in the range of 5 µm to 40 µm from the center of the first recess 128 may be defined as the boundary position. However, the boundary position may be varied according to a level of an injected current and the Al composition.

A current density is low in a low current density region P3 between the first electrodes 142 such that the low current density region P3 hardly contributes to the light emission. Therefore, according to the present embodiment, the reflective layer is formed in the low current density region such that extraction efficiency of light can be improved.

However, it is inefficient to form the reflective layer across an entire area of the low current density region P3. Therefore, it may be advantageous to increase optical power by leaving only a region in which the reflective layer will be formed and by possibly densely disposing the first electrodes in the remaining region.

Referring to FIG. 7A, the reflective layer 135 may include an inclined part 135b and an upper part 135c. Most of the light emitted from the active layer 124 may be reflected upward by the inclined part 135b.

The first region 136 defined by the reflective layer 135 may have an area of 2.0 to 5.0 times that of the first electrode 142. In this case, the reflective layer 135 may be formed in a region in which a current density is 40% or less relative to the current density of the first electrode 142. Alternatively, the first region 136 defined by the reflective layer 135 may have an area of 2.0 to 5.0 times that of the first recess 128. The area of the first region 136 may be adjusted according to the Al concentration of the semiconductor structure 120.

Referring to FIG. 7B, a spacing T1 between adjacent first recesses may be the sum of a distance T2 from the center of the first recess to the second electrode and the distance S1 between the second electrodes. As described above, the distance S1 between the second electrodes needs to be secured at least 3 µm or more.

The sum of areas of the plurality of first recesses 128 may be in the range of 12% to 24% relative to a maximum horizontal area of the semiconductor structure. When the sum of the areas of the plurality of first recesses is greater than 24%, the spacing T1 between the first recesses becomes narrower. Consequently, the distance S1 between the second electrodes may not be secured. When the sum of the areas of the plurality of first recesses is less than 12%, an area of an n-type electrode becomes smaller such that sufficient current distribution becomes difficult.

For example, when the sum of the areas of the plurality of first recesses is 12%, the spacing T1 between the first recesses may be 130 µm and the distance T2 from the center of the first recess to the second electrode may be 63.5 Therefore, a spacing of about 3 µm may be secured for forming the reflective layer.

Further, when the sum of the areas of the plurality of first recesses is 24%, the spacing T1 between the first recesses may be 101 µm and the distance T2 from the center of the first recess to the second electrode may be 49 µm. Therefore, a spacing of about 3 µm may be secured for forming the reflective layer of the first recess.

Referring to FIG. 8, as the number of first recesses increases or the distance S1 between the second electrodes becomes wider, the areas of the plurality of second electrodes 146 are decreased.

The semiconductor structure 120 may include a plurality of first regions 136 separated by the second recesses 127 and a second region 137 defined between a lateral surface E1 of the semiconductor structure 120 and the second recess 127. The separation distance S1 between the first regions 136 may be equal to or wider than the width of the second recess 127.

The plurality of second electrodes 146 may include a plurality of sub-electrodes 147 disposed within the first region 136 and an edge electrode 148 disposed within the second region 137.

The plurality of sub-electrodes 147 may be disposed between the first recesses and the second recesses. The plurality of sub-electrodes 147 are separated from one another but may be electrically connected to one another by the reflective layers.

The edge electrode 148 may be continuously disposed along an edge of the semiconductor structure 120. However, the present invention is not particularly limited thereto, and the edge electrode 148 may be divided into a plurality of edge electrodes. Alternatively, the edge electrode 148 may be omitted.

A separation distance d1 between the second recess 127 and the lateral surface E1 of the semiconductor structure 120 may be in the range of 1.0 µm to 10 µm. When the separation distance d1 is shorter than 1.0 µm, it is difficult to secure a process margin. Further, when the separation distance d1 is longer than 10 µm, an area involved in light emission is reduced such that extraction efficiency of the light may be degraded. However, the present invention is not particularly limited thereto, and the second recess 127 and the reflective layer may be formed up to the lateral surface E1 of the semiconductor structure 120. In this case, the edge electrode 148 may be divided into a plurality of edge electrodes.

Figure 9:
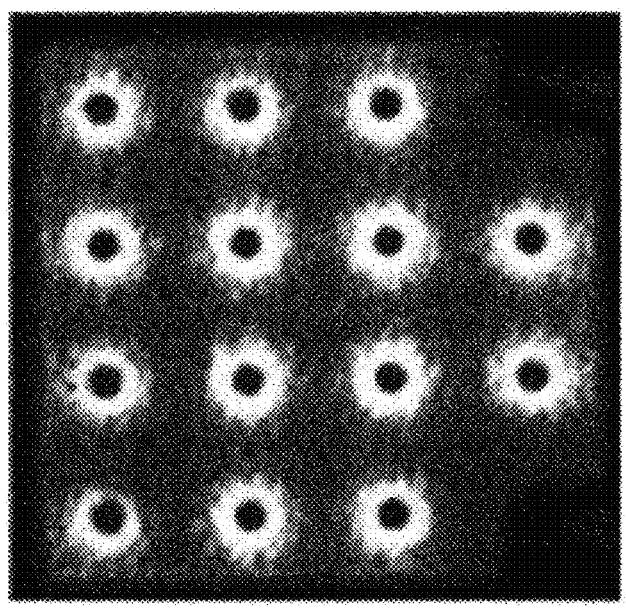
FIG. 9 is a photograph of a semiconductor device according to a first embodiment of the present invention.
Figure 10:
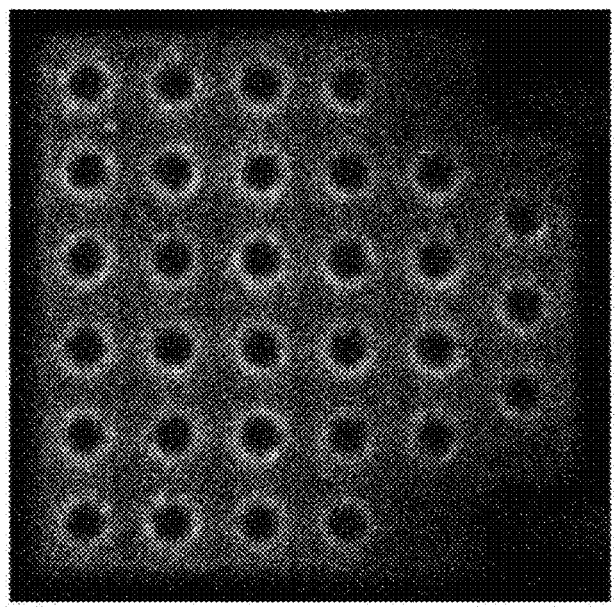
FIG. 10 is a photograph of a semiconductor device according to a second embodiment of the present invention.
Figure 11:
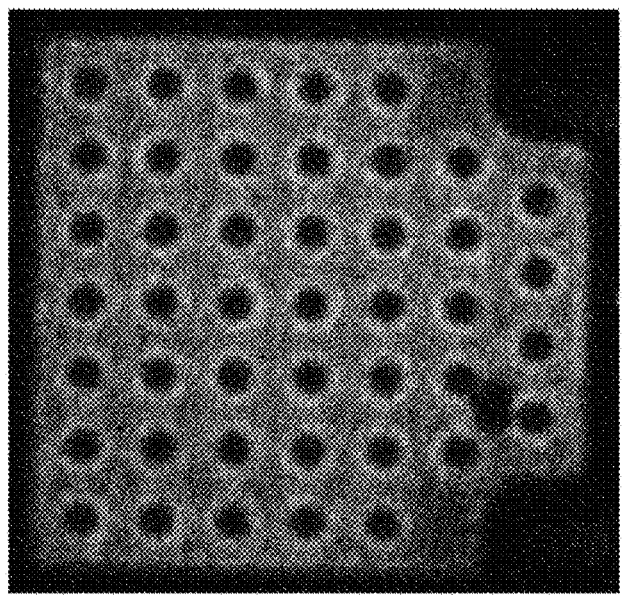
FIG. 11 is a photograph of a semiconductor device according to a third embodiment of the present invention.
Figure 12:
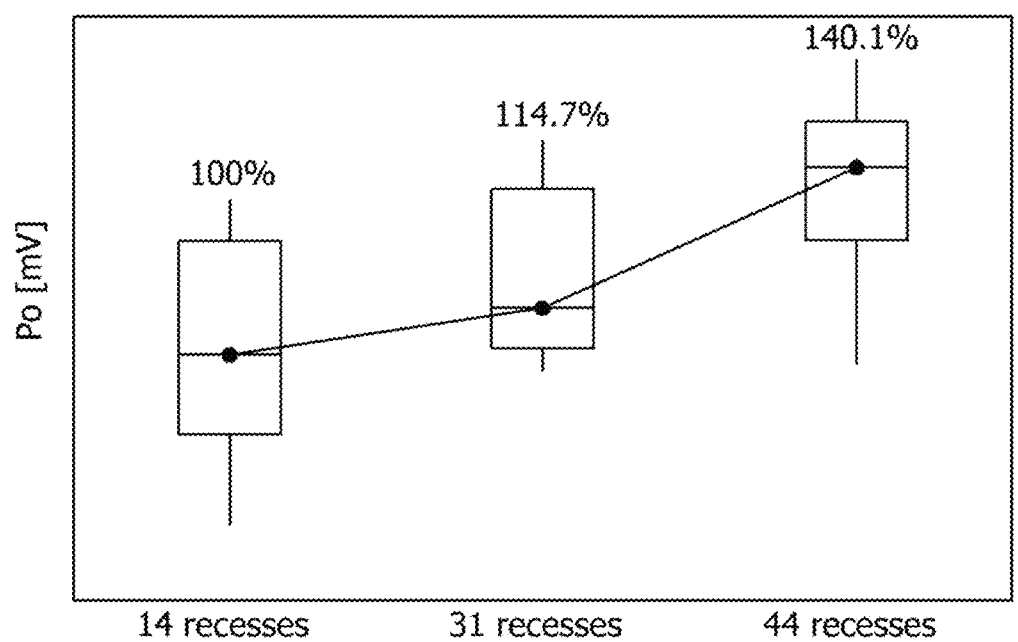
FIG. 12 is a graph showing optical power of the semiconductor devices according to the first to third embodiments.
Figure 13:
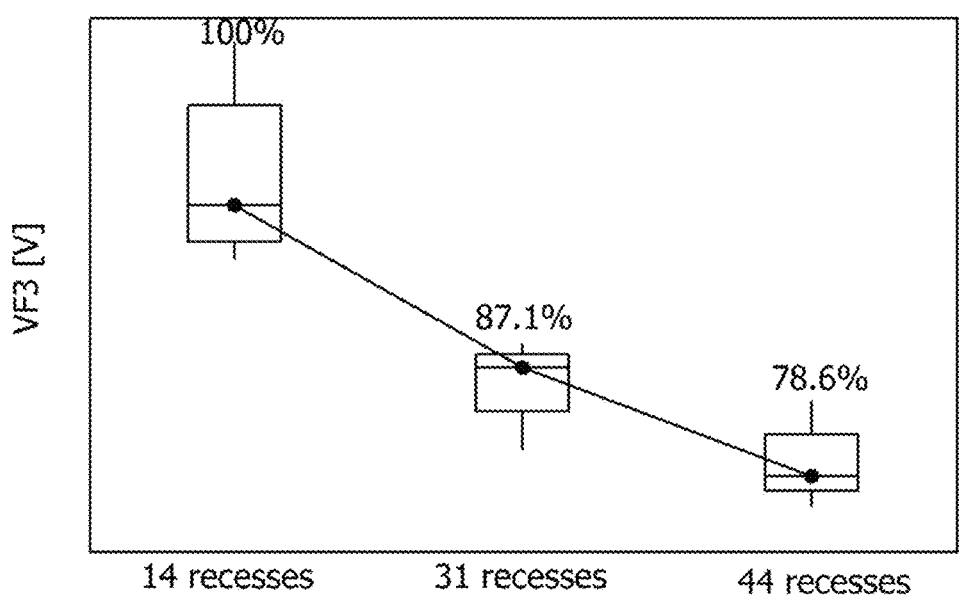
FIG. 13 is a graph showing operating voltages of the semiconductor devices according to the first to third embodiments.

FIG. 9 is a photograph of a semiconductor device according to a first embodiment of the present invention, FIG. 10 is a photograph of a semiconductor device according to a second embodiment of the present invention, FIG. 11 is a photograph of a semiconductor device according to a third embodiment of the present invention, FIG. 12 is a graph showing optical power of the semiconductor devices according to the first to third embodiments, and FIG. 13 is a graph showing operating voltages of the semiconductor devices according to the first to third embodiments.

Referring to FIG. 9, when the first recesses are 14, it can be confirmed that only peripheries of the first electrodes emit light and the remaining portions hardly emit light. Referring to FIG. 10, when the number of first recesses increases to 31, it can be seen that a light emitting area becomes wider than that of FIG. 9. Further, referring to FIG. 11, it can be confirmed that light is entirely emitted as compared with FIG. 10. That is, as the areas of the first electrodes increase, a current distribution characteristic is improved such that most of the active layers are involved in the light emission.

Referring to FIG. 12, it can be confirmed that optical power of the second embodiment in which the number of first recesses 128 is 31 was improved to 114.7% relative to 100% optical power of the first embodiment in which the number of first recesses 128 is 14. Further, when the number of holes is 44, it can be confirmed that the optical power is improved to 140.1%. That is, it can be seen that a total area of the active layers is reduced, but areas of the active layers involved in the light emission are increased.

Referring to FIG. 13, it can be confirmed that an operating voltage of the second embodiment in which the number of first recesses 128 is 31 dropped to 87% relative to a 100% operating voltage of the first embodiment in which the number of first recesses 128 is 14. Further, when the number of holes is 44, it can be confirmed that the operating voltage further dropped to 78%. That is, it can be confirmed that the total area of the first electrodes is increased and the current distribution characteristic is improved such that the operating voltage dropped.

Figure 14:
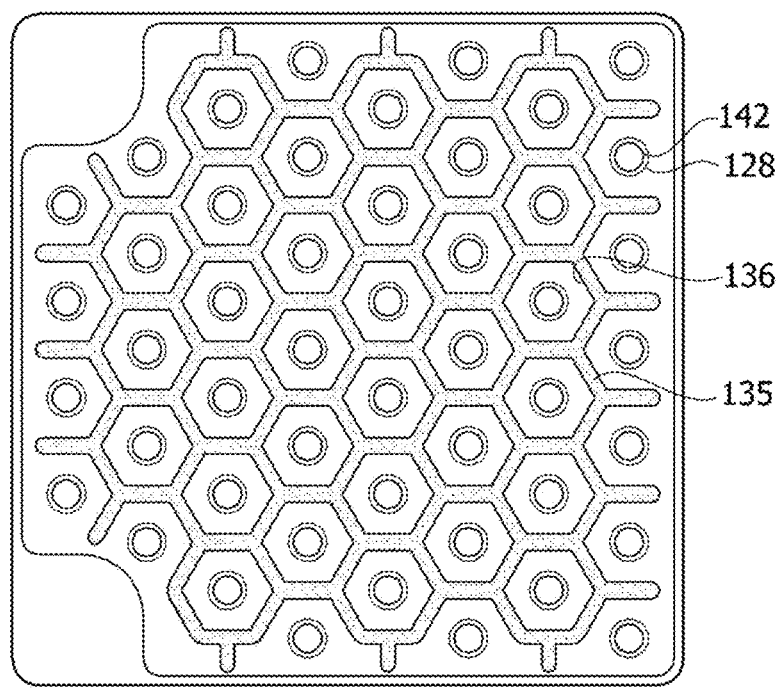
FIG. 14 is a diagram illustrating a semiconductor device according to a fourth embodiment of the present invention.
Figure 15:
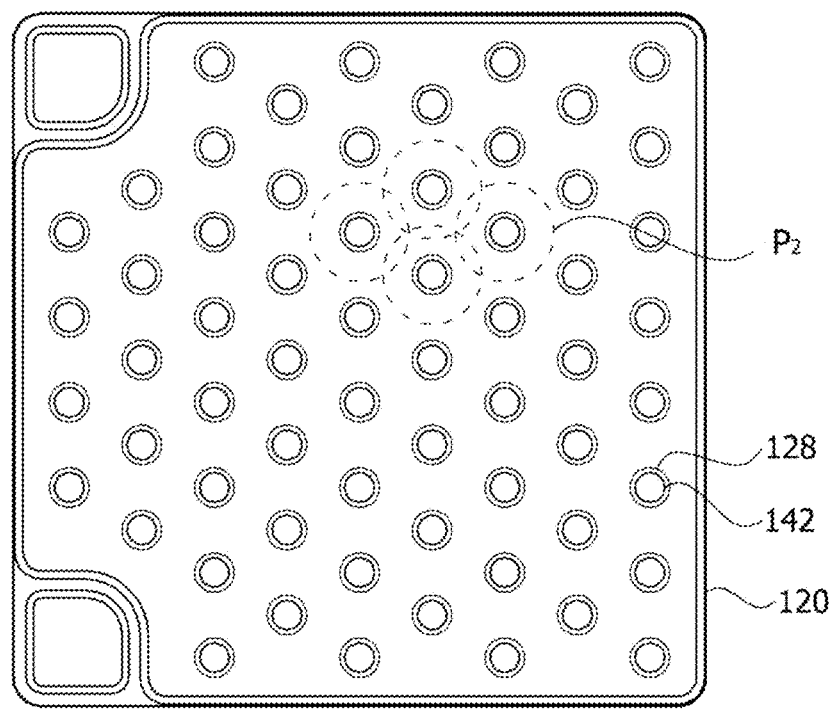
FIG. 15 is a diagram illustrating a semiconductor device according to a fifth embodiment of the present invention.
Figure 16:
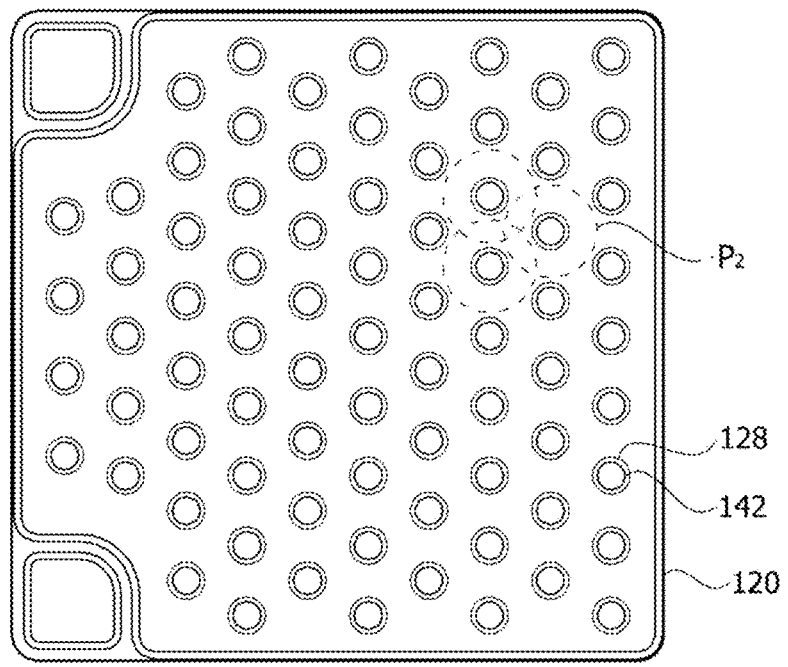
FIG. 16 is a diagram illustrating a semiconductor device according to a sixth embodiment of the present invention.
Figure 17:
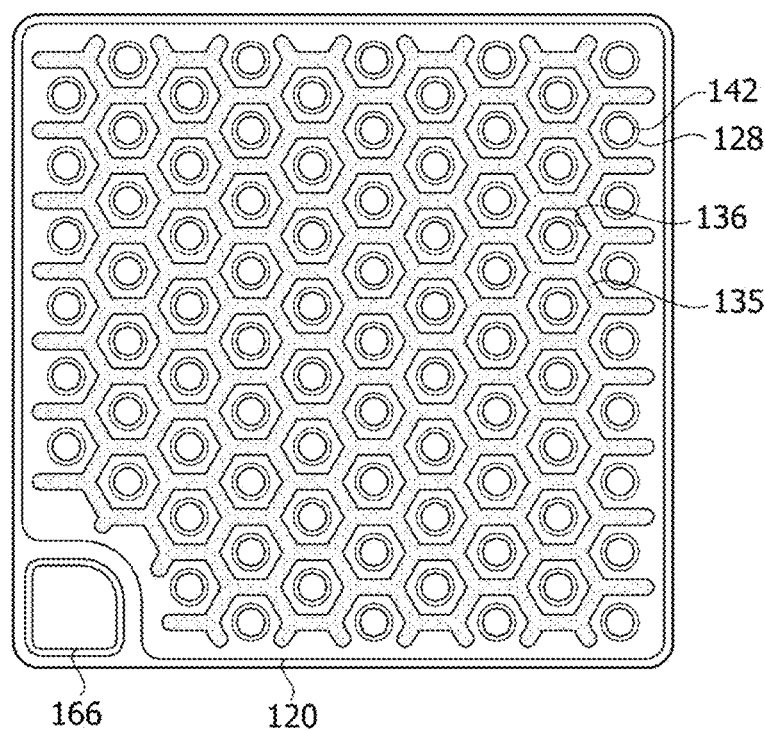
FIG. 17 is a diagram illustrating a semiconductor device according to a seventh embodiment of the present invention.
Figure 18:
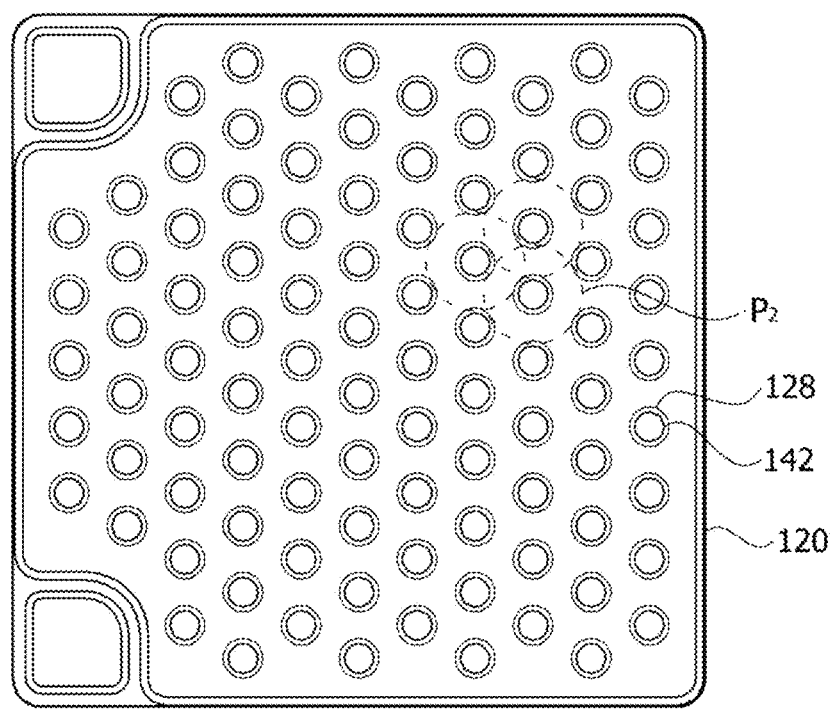
FIG. 18 is a diagram illustrating a semiconductor device according to an eighth embodiment of the present invention.
Figure 19:
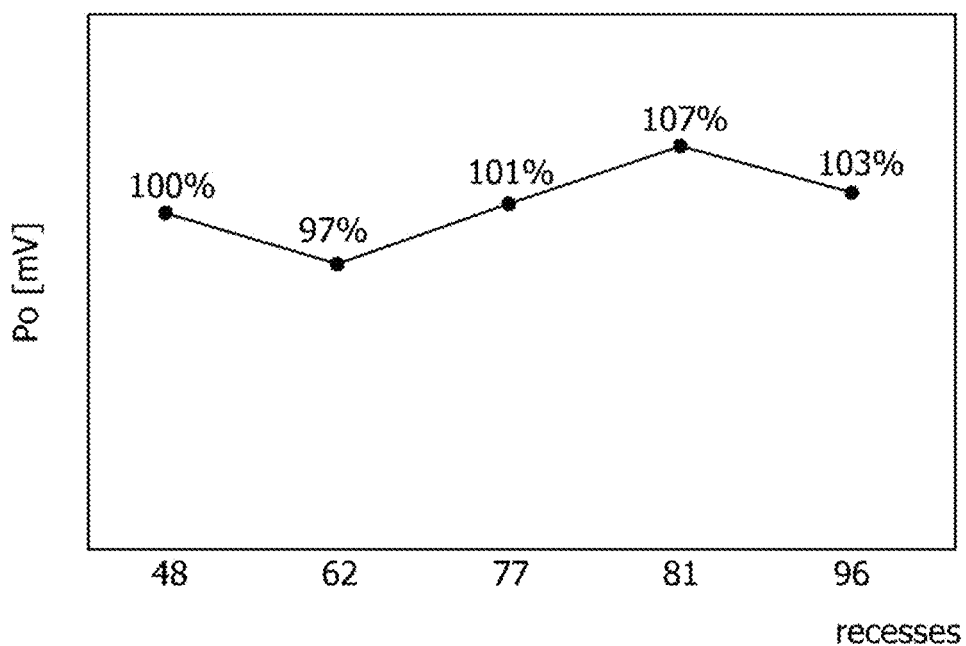
FIG. 19 is a graph showing optical power of the semiconductor devices according to the fourth to eighth embodiments.
Figure 20:
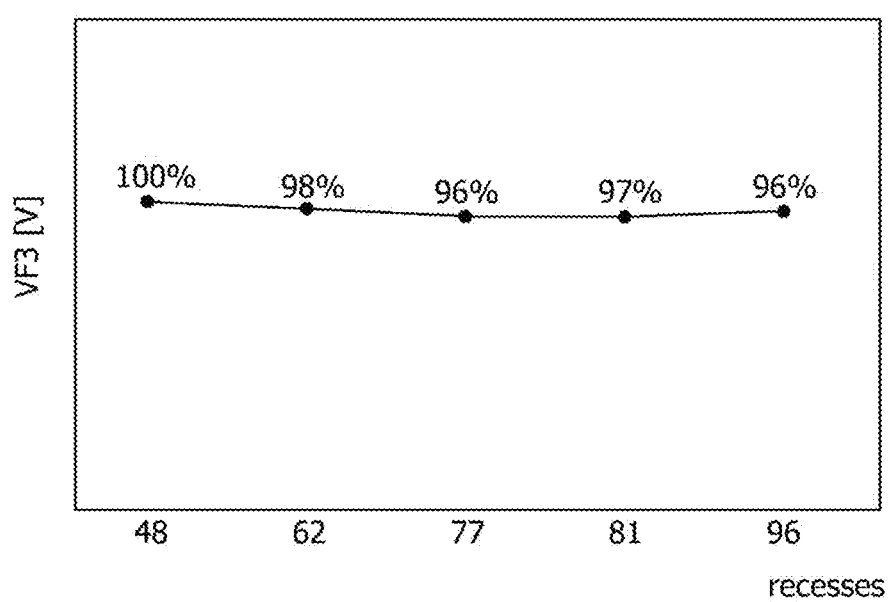
FIG. 20 is a graph showing operating voltages of the semiconductor devices according to the fourth to eighth embodiments.

FIG. 14 is a diagram illustrating a semiconductor device according to a fourth embodiment of the present invention, FIG. 15 is a diagram illustrating a semiconductor device according to a fifth embodiment of the present invention, FIG. 16 is a diagram illustrating a semiconductor device according to a sixth embodiment of the present invention, FIG. 17 is a diagram illustrating a semiconductor device according to a seventh embodiment of the present invention, FIG. 18 is a diagram illustrating a semiconductor device according to an eighth embodiment of the present invention, FIG. 19 is a graph showing optical power of the semiconductor devices according to the fourth to eighth embodiments, and FIG. 20 is a graph showing operating voltages of the semiconductor devices according to the fourth to eighth embodiments.

The following Table 1 shows an active layer area, a p-ohmic electrode area (a second area), a recess area, an n-ohmic electrode area (a first area), and the number of first recesses of the fourth to eighth embodiments.

The active layer area may be a mesa etched area of the semiconductor structure and may be an area ratio of the active layer to the maximum horizontal area of the semiconductor structure. Where the area of the semiconductor structure may be a maximum cross-sectional area in a horizontal direction by adding the mesa etched area to the recessed area.

The p-electrode area is an area ratio of the second electrode to a maximum area of the semiconductor structure in the horizontal direction.

The n-electrode area is an area ratio of the first electrode to the maximum area of the semiconductor structure in the horizontal direction.

The fourth and seventh embodiments were tested by forming the reflective layer, and the fifth, sixth, and eighth embodiments were tested without forming the reflective layer.

TABLE 1

| | Active layer area [%] | P-electrode area [%] | Spacing between p-electrodes [μm] | N-electrode area [%] | Area ratio (n-electrode: p-electrode) | The number of recesses | Presence or absence of reflective layer |
|---|---|---|---|---|---|---|---|
| Fourth embodiment | 66.5 | 57 | 56 | 6 | 1:9.5 | 48 | Y |
| Fifth embodiment | 67.7 | 51 | 40 | 7.8 | 1:6.5 | 62 | — |
| Sixth embodiment | 66.4 | 44 | 31 | 9.7 | 1:4.5 | 77 | — |
| Seventh embodiment | 61.9 | 41 | 29 | 10.2 | 1:4.0 | 81 | Y |
| Eight embodiment | 58.1 | 39.8 | 19 | 12.1 | 1:3.2 | 96 | N |

Referring to FIGS. 14 to 18 and Table 1, it can be seen that as the number of first recesses increases, the effective light emitting regions P2 overlap. Therefore, a total active layer area is reduced, but most of the active layers may be involved in the light emission.

The first area in which the plurality of first electrodes 142 are in contact with the first conductive semiconductor layer 122 may be in the range of 6.0% to 11% relative to the maximum cross-sectional area of the semiconductor structure 120 in the horizontal direction. The first area may be the sum of areas in which the first electrodes 142 are in contact with the first conductive semiconductor layer 122.

When the first area of the plurality of first electrodes 142 is less than 6.0%, a current distribution characteristic is not sufficient such that the optical power is reduced, whereas when the first area of the plurality of first electrodes 142 exceeds 11%, the spacing between the second electrodes is excessively reduced such that it is difficult to secure a space in which the reflective layer will be formed. In this case, in order to form the first area in the range of 6.0% to 11%, the areas of the plurality of first recesses may be in the range of 12% to 24% relative to the maximum area of the semiconductor structure in the horizontal direction.

As the result of the test, the fourth to seventh embodiments secured the space, in which the reflective layer will be formed, between the second electrodes, but the eighth embodiment did not secure the space in which the reflective layer including the extension part will be formed.

The second area in which the second electrode 246 is in contact with the second conductive semiconductor layer 126 may be in the range of 40% to 60% relative to the maximum cross-sectional area of the semiconductor structure 120 in the horizontal direction. The second area may be a total area in which the second electrodes 246 are in contact with the second conductive semiconductor layers 126.

When the second area is less than 40%, an area of the second electrode becomes excessively smaller such that there is a problem in that the operating voltage rises and hole injection efficiency is lowered. When the second area exceeds 60%, the first area cannot be effectively widened such that there is a problem in that electron injection efficiency is lowered.

The second area may be equal to or less than a remaining area except for the areas of the plurality of first recesses and the plurality of second recesses formed on the lower surface of the semiconductor structure. Accordingly, a third area which is the sum of the areas of the plurality of first recesses and the plurality of the second recesses may be 60% or less relative to the maximum area of the semiconductor structure in the horizontal direction.

When the third area is 60% or more relative to the maximum area of the semiconductor structure in the horizontal direction, the area of the second electrode becomes too small such that it is difficult to form the reflective layer. Further, there is a problem in that the operating voltage rises and hole injection efficiency is degraded.

The areas of the plurality of second recesses may be in the range of 4.8% to 5.7% relative to the maximum area of the semiconductor structure in the horizontal direction. When the areas of the plurality of second recess are less than 4.8%, it is difficult to form the reflective layer, whereas when the areas of the plurality of second recess are greater than 5.7%, the second area becomes smaller such that the operating voltage rises.

The first area and the second area have an inverse relationship. That is, when the number of the first recesses is increased in order to increase the number of the first electrodes, the area of the second electrode is decreased. To increase the optical power, a distribution characteristic of electrons and holes should be balanced. Further, in order to form the reflective layer, it is important to appropriately determine a ratio of the first area to the second area.

An area ratio of the first area in which the plurality of first electrodes are in contact with the first conductive semiconductor layer to the second area in which the plurality of second electrodes are in contact with the second conductive semiconductor layer (the first area:the second area) may be preferably controlled to be 1:4 or more. When the area ratio is less than 1:4, it is difficult to secure the space in which the reflective layer will be formed as in the eighth embodiment.

Further, when the area ratio is greater than 1:10, the first area becomes relatively smaller as in the first and second embodiments such that the current distribution characteristic may be degraded. For example, in the case of the first embodiment, it was confirmed that the first area was merely about 1.8% such that current injection efficiency was significantly poor. Consequently, light is emitted from only the regions in the vicinity of the first electrodes.

According to the exemplary embodiments, an area ratio of the first recess 128 to the first region 136 may be in the range of 1:4 to 1:8. When the area ratio is less than 1:4, the number of the first recesses 128 increases such that it is difficult to secure the space in which the reflective layer 135 will be formed. Further, when the area ratio is greater than 1:8, an area of an n-electrode becomes relatively smaller such that the current distribution characteristic may be degraded.

In the fourth embodiment, the area ratio of the first recess 128 to the first region 136 is 1:8, and in the seventh embodiment, the area ratio of the first recess 128 to the first region 136 is 1:4. In this case, since radii of the first recesses are the same, it can be seen that as the number of the first recesses increases, the area of the first region becomes narrower gradually. Here, the area of the first region 136 is a total area including the first recess.

Referring to FIG. 19, it can be confirmed that optical power of the fifth embodiment in which the number of the first recesses is 62 was reduced relative to 100% optical power of the fourth embodiment in which the number of first recesses is 48. That is, it can be confirmed that the extraction efficiency of the light is improved by the reflective layer as in the fourth embodiment.

Similarly, in the seventh embodiment in which the number of the first recesses is 81 and the reflective layer is formed, it can be seen that the optical power is higher than that of the eighth embodiment in which the number of the first recesses is 96 without forming the reflective layer.

Referring to FIG. 20, even when the number of the first recesses was increased from 48 to 96, the operating voltage did not significantly vary.

Figure 21:
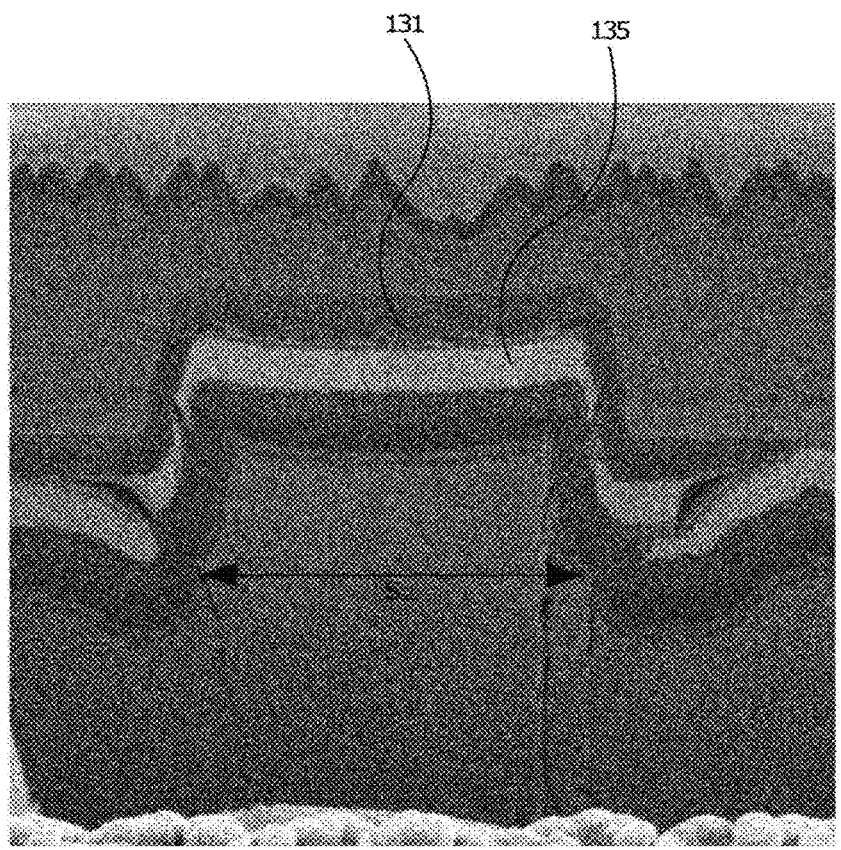
FIG. 21 is a scanning electron microscope (SEM) photograph showing a cross section of the eighth embodiment of the present invention.

Referring to FIG. 21, in the case of the eighth embodiment, when the width S2 of the reflective layer 135 is about 4.5 µm, it can be confirmed that cracks occur at the reflective layer 135. Therefore, when the width of the second recess becomes narrower to about 4.5 µm or less, it can be confirmed that it is difficult to form the reflective layer.

However, when the inclination angle is adjusted to be smaller, the width of the reflective layer may be controlled to about 3.0 µm. Therefore, it is preferable that the width S2 of the reflective layer is formed to be wider than about 3.0 µm.

Figure 22:
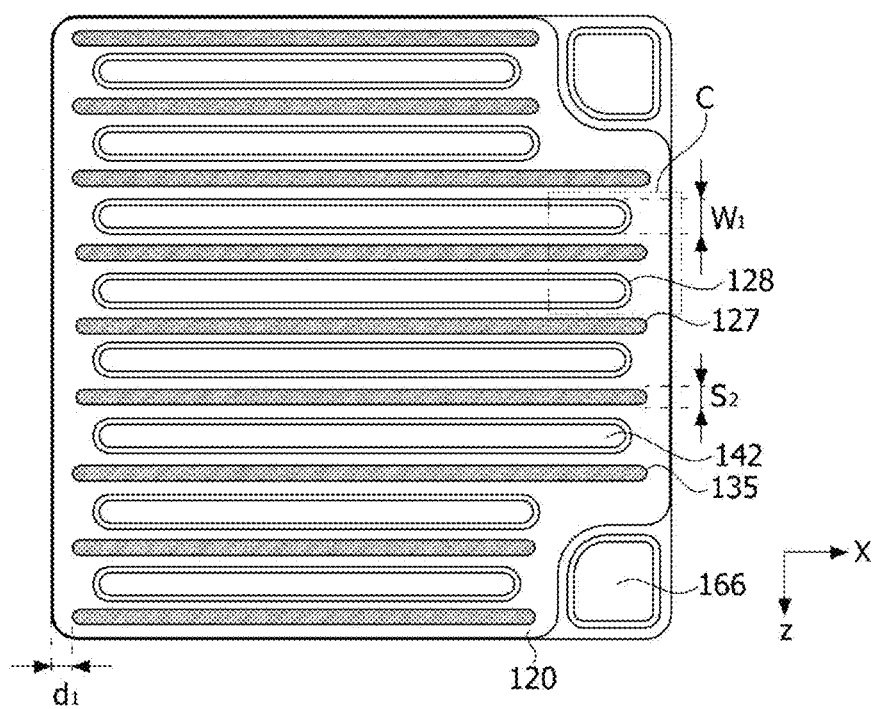
FIG. 22 is a plan view of a semiconductor device according to a ninth embodiment of the present invention.
Figure 23:
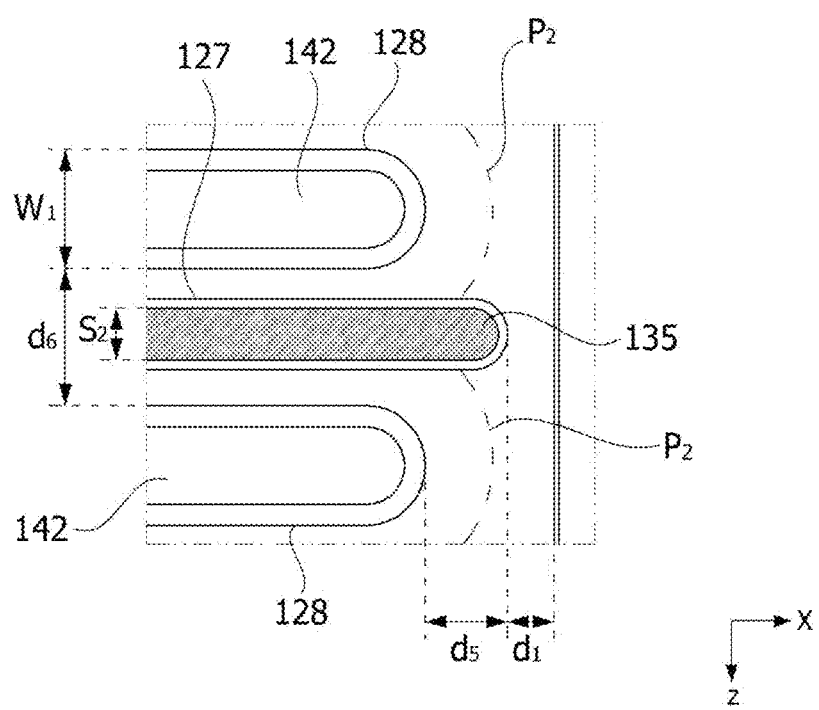
FIG. 23 is an enlarged view of Portion C of FIG. 22.
Figure 24:
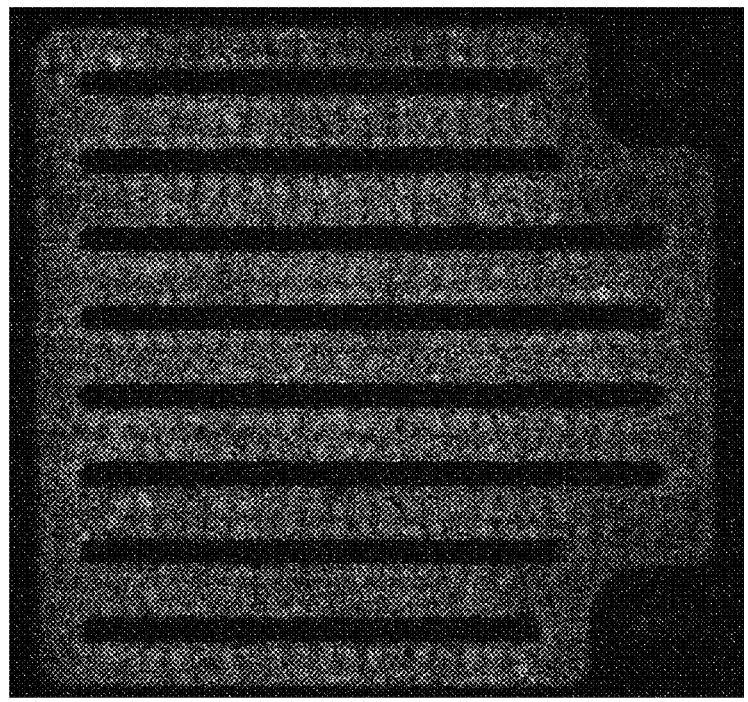
FIG. 24 is a photograph of a light emitting structure to which power is applied.

FIG. 22 is a plan view of a semiconductor device according to a ninth embodiment of the present invention, FIG. 23 is an enlarged view of Portion C of FIG. 22, and FIG. 24 is a photograph of a light emitting structure to which power is applied.

Referring to FIGS. 22 and 23, a first recess 128 may extend in a first direction (an X-direction) and may be disposed and spaced apart in a second direction (a Z-direction). Here, the first direction may be a direction perpendicular to a thickness direction (a Y-direction) of a light emitting structure 120. Hereinafter, a width (area) of each of the first recess 128 and a second recess 127 is defined as an area formed at a lower portion of the light emitting structure 120.

A first electrode 142 may be disposed inside the first recess 128. An area of the first electrode 142 may be controlled by adjusting the number of first recesses 128 or adjusting a length of the first recess 128 extending in the first direction.

Since a current distribution is not relatively easy in a UV light emitting structure having a high Al concentration, an area of the first electrode needs to be wider than that of a GaN light emitting structure which emits blue light. In the present embodiment, a plurality of first electrodes 142 are in contact with a first conductive semiconductor layer in the first direction such that an current injection area may become wider.

In this case, when the first recess 128 is excessively formed so as to widen the area of the first electrode 142, areas of an active layer 124 and a second electrode 146 are decreased such that it is important to maintain an appropriate area ratio.

A width W1 of the first recess 128 may be in the range of 30 µm to 60 µm. When the width W1 of the first recess 128 is less than 30 µm, it is difficult to secure a process margin for forming the first electrode 142 inside the first recess 128, whereas when the width W1 is greater than 60 µm, the active layer is excessively reduced such that optical power may be lowered.

A distance d6 between the first recesses 128 may be in the range of 20 µm and 60 µm. When the distance d6 is less than 20 µm, the active layer is excessively reduced such that the optical power may be lowered, whereas when the distance d6 is greater than 60 µm, the number of the first recesses 128 is decreased such that it is difficult to sufficiently secure the area of the first electrode 142.

The areas of the plurality of first electrodes 142 may be in the range of 19% to 29% relative to a 100% maximum area of the light emitting structure 120 in the first direction. When the areas of the plurality of first electrodes 142 are less than 19%, sufficient current injection and diffusion may be difficult, whereas when the areas of the plurality of first electrodes 142 are greater than 29%, an area in which the active layer 124 and the second electrode 146 will be disposed is reduced such that there is a problem in that the optical power is lowered and the operating voltage rises.

The areas of the plurality of first recesses 128 may be in the range of 30% to 45% relative to the 100% maximum area of the light emitting structure 120 in the first direction. When the areas of the plurality of first recesses 128 are less than 30%, there is a problem in that the area of the first electrode 142 is reduced, whereas when the areas of the plurality of first recesses 128 are greater than 45%, the area in which the active layer 124 and the second electrode 146 will be disposed is reduced such that there is a problem in that the optical power is lowered and the operating voltage rises.

A plurality of second recesses 127 may extend in the first direction (the X-direction) and may be disposed and spaced apart in the second direction (the Y-direction). The second recess 127 may be disposed between the plurality of first recesses 128.

A reflective layer 135 may be disposed inside the second recess 127. Accordingly, the reflective layer 135 may be disposed on both sides of each of the plurality of first electrodes 142 to reflect the light emitted in the vicinity of the first electrode 142 upward. A width S2 of the reflective layer 135 may be equal to or wider than a width of the second recess 127.

As an Al composition becomes higher, a current distribution effect may be degraded. Accordingly, a current is distributed only in the vicinity of the first electrode 142 such that a current density may be drastically lowered at a position away from the first electrode 142. Therefore, an effective light emitting region P2 becomes narrower.

The effective light emitting region P2 may be defined as a boundary position at which a current density is in the range of 30% to 40% relative to a center of the first electrode 142 at which a current density is 100%. For example, a distance separated in the range of 5 μm to 40 μm from a center of the first recess 128 in the second direction may be defined as the boundary position. However, the boundary position may be varied according to a level of an injected current and an Al concentration.

The reflective layer 135 may be disposed at the boundary position in which the current density is in the range of 30% to 40%. That is, according to the present embodiment, the reflective layer 135 is formed in a low current density region such that extraction efficiency of light may be improved.

A length of the second recess 127 in the first direction may be formed to be longer than a length of an adjacent first recess 128 in the first direction. When the length of the second recess 127 is equal to or shorter than that of the adjacent first recess 128, light emitted from an end position of the first recess 128 cannot be controlled.

Here, the first recess 128 adjacent to the second recess 127 may be two first recesses 128 disposed closest to the second recess 127 in the second direction (the Z-direction). That is, the second recess 127 may be formed to be longer than at least one of the two first recesses 128 disposed adjacent to the second recess 127 in left and right sides.

One end of the second recess 127 may be disposed to be longer than one end of the first recess 128 (d5). The length of the second recess 127 in the first direction may be 104% or more relative to a length of one of the adjacently disposed first recesses 128 in the first direction. In this case, the light emitted in the vicinity of both ends of the first electrode 142 may be effectively reflected upward.

A separation distance d1 between the second recess 127 and a lateral surface of the light emitting structure 120 may be in the range of 1.0 μm to 10 μm. When the separation distance d1 is less than 1.0 μm, it is difficult to secure the process margin and thus a capping layer 150 is difficult to be disposed to surround the reflective layer 135 such that reliability may be degraded. Further, when the separation distance d1 is longer than 10 μm, an area involved in light emission is reduced such that extraction efficiency of the light may be degraded. However, the present invention is not particularly limited thereto, and the second recess 127 and the reflective layer 135 may be formed up to the lateral surface of the light emitting structure 120.

The areas of the plurality of second recesses 127 may be in the range of 4% to 10% relative to the 100% maximum area of the light emitting structure 120 in the first direction. When the areas of the plurality of second recesses 127 are less than 4%, it is difficult to form the reflective layer 135 inside the second recess 127. Further, when the areas of the plurality of second recesses 127 are greater than 10%, an area of the active layer is reduced such that the optical power may be lowered.

The area of the reflective layer 135 may be in the range of 46% to 70% relative to the 100% maximum area of the light emitting structure 120 in the first direction. A region of the reflective layer 135 which actually reflects the light may be equal to or less than the area of the second recess 127. Here, the area of the reflective layer 135 is an area including an extension part extending to a lower surface of the light emitting structure 120 to cover the second electrode 146.

An area of the second electrode 146 may be in the range of 57% to 86% relative to the 100% maximum area of the light emitting structure 120 in the first direction. When the area of the second electrode 146 is less than 57%, the operating voltage may rise, whereas when the area of the second electrode 146 is greater than 86%, the area of the first electrode 142 is reduced such that efficiency of current injection and distribution may be lowered.

The area of the second electrode 146 may be a remaining area except for the areas of the first recess 128 and the second recess 127 in the light emitting structure 120. Thus, the second electrode 146 may be a single electrode which is entirely connected.

Figure 25:
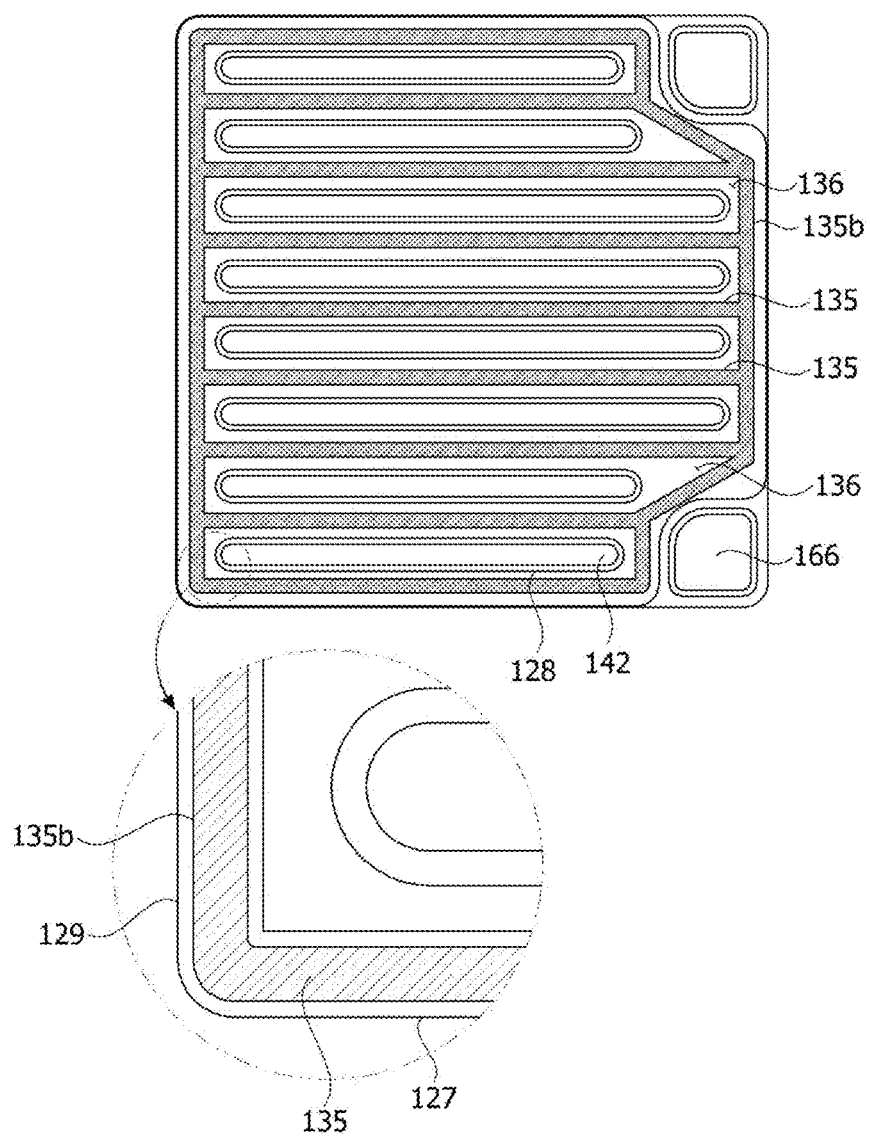
FIG. 25 is a plan view of a semiconductor device according to a tenth embodiment of the present invention.
Figure 26A:
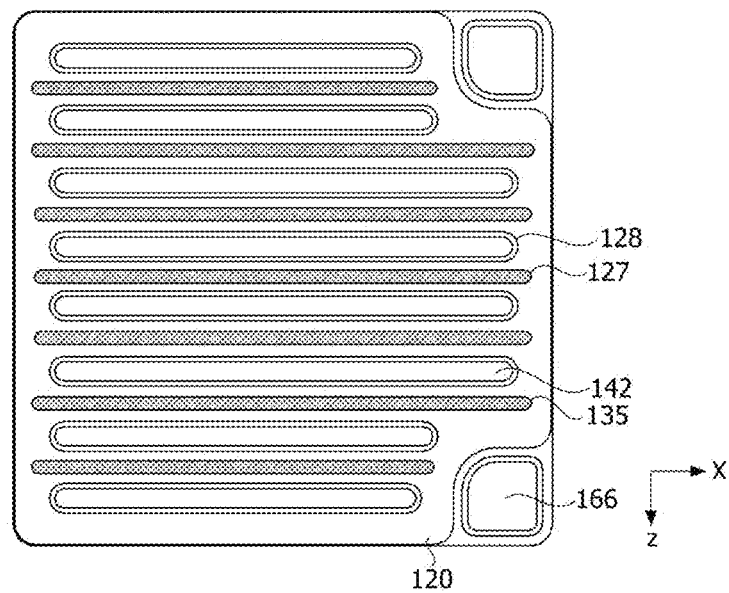
FIGS. 26A and 26B are diagrams illustrating a semiconductor device according to an eleventh embodiment of the present invention.
Figure 26B:
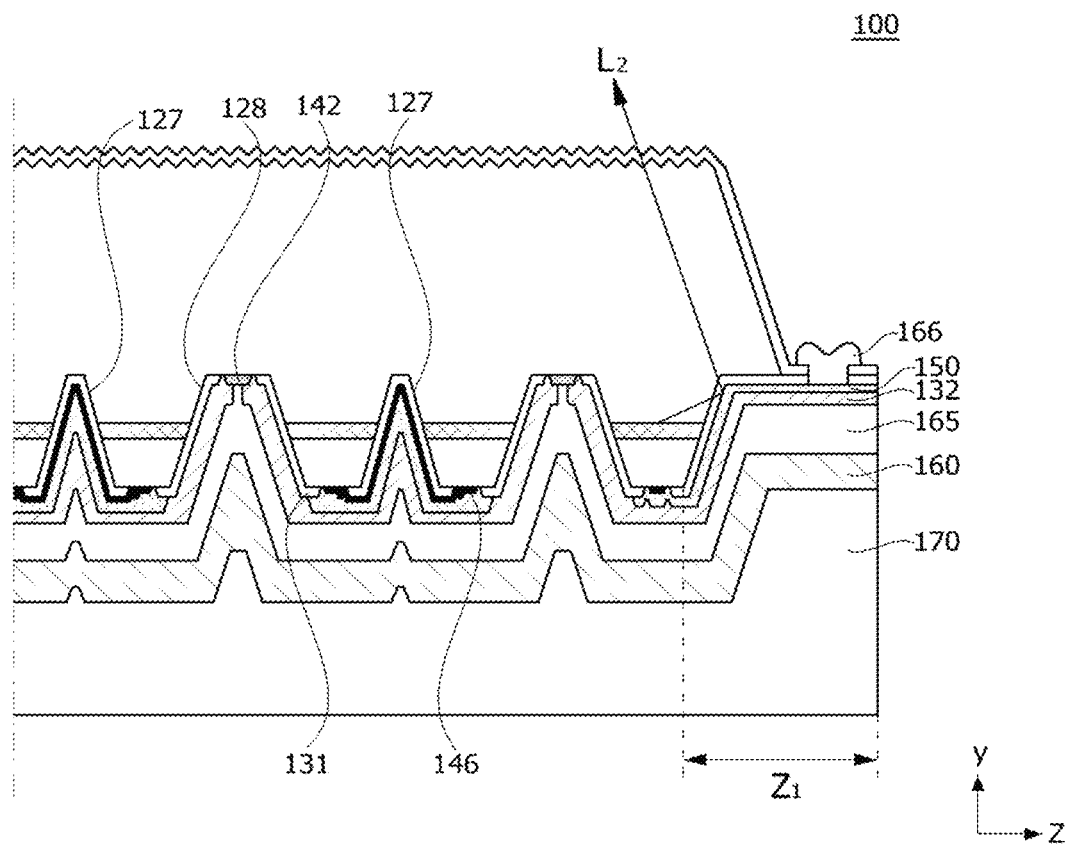
Figure 27:
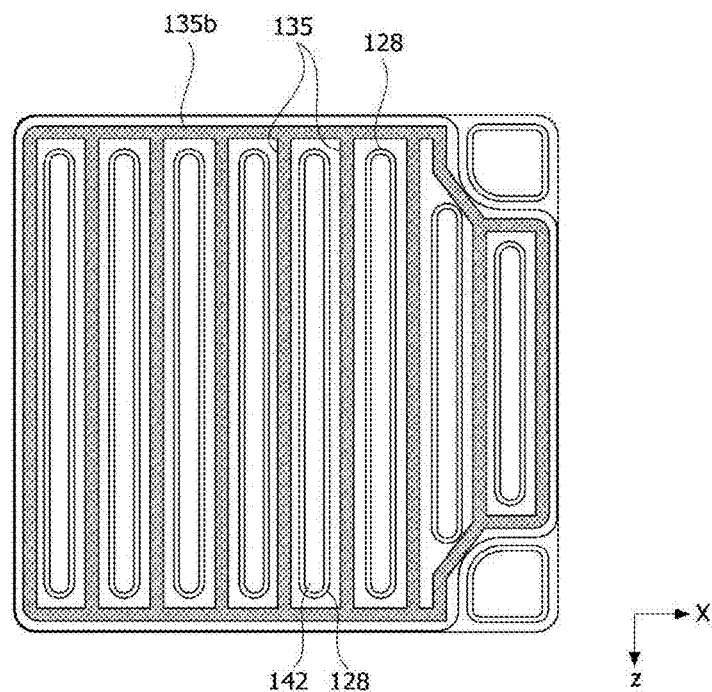
FIG. 27 is a diagram illustrating a semiconductor device according to a twelfth embodiment of the present invention.
Figure 28:
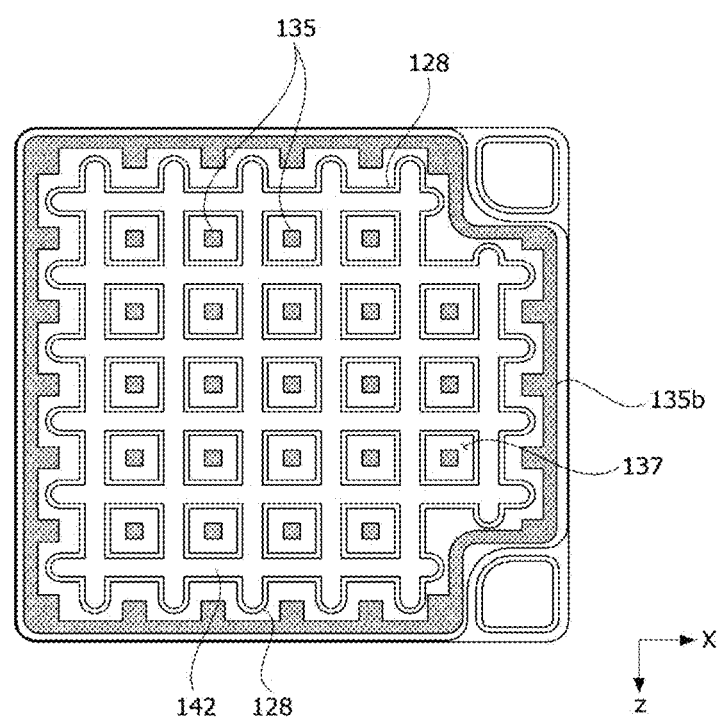
FIG. 28 is a diagram illustrating a semiconductor device according to a thirteen embodiment of the present invention.

FIG. 25 is a plan view of a semiconductor device according to a tenth embodiment of the present invention, FIGS. 26A and 26B are diagrams illustrating a semiconductor device according to an eleventh embodiment of the present invention, FIG. 27 is a diagram illustrating a semiconductor device according to a twelfth embodiment of the present invention, and FIG. 28 is a diagram illustrating a semiconductor device according to a thirteen embodiment of the present invention.

Referring to FIG. 25, the semiconductor device may include a lateral reflection part 135b connected to both ends of each of a plurality of reflective layers 135. That is, a third recess 129 may be formed at an edge of a light emitting structure 120, and the lateral reflection part 135b may be formed inside the third recess 129. The reflective layer 135 and the lateral reflection part 135b may include the same reflective material. For example, the reflective layer 135 and the lateral reflection part 135b may contain Al.

The plurality of reflective layers 135 and the lateral reflection parts 135b may be electrically connected or may be spaced apart from each other.

When the plurality of reflective layers 135 and the lateral reflection parts 135b are connected to each other, a plurality of first regions 136 may be formed. The plurality of first regions 136 may be spaces separated from one another by the plurality of reflective layers 135.

A first recess 128 and a first electrode 142 may be disposed in each of the plurality of first regions 136. According to the above-described configuration, light emitted in the vicinity of both ends of the first electrode 142 may be effectively reflected upward.

A second electrode may be separated into a plurality of second electrodes by a second recess 127 and the third recess. The plurality of separated second electrodes 146 may be electrically connected to one another by an extension part of the reflective layer 135.

Referring to FIG. 26A, a reflective layer 135 may not be disposed at an edge of a light emitting device. That is, owing to various reasons such as a process margin and the like, the reflective layer 135 or a first electrode 142 may be disposed at the edge.

Referring to FIG. 26B, a capping layer 150, a lower electrode layer 165, and a substrate 70 protrude from an edge portion Z1 of the semiconductor device to reflect light L2 emitted from an active layer 124 upward. That is, a lateral reflection portion may be formed on the edge portion Z1 of the semiconductor device. Therefore, the light emitted from an outermost periphery may be reflected upward without forming a separate reflective layer.

An angle θ4 between the capping layer 150 and a lower surface of a second conductive semiconductor layer 126 may be in the range of 90 degrees to 145 degrees. When the angle is less than 90 degrees or greater than 145 degrees, efficiency of reflecting the light traveling toward a lateral surface upward may be lowered.

According to the above-described configuration, light emitted between a plurality of first recesses 128 may be reflected upward by the reflective layer 135, and light emitted from an edge of a light emitting structure 120 may be reflected upward by the capping layer 150.

Referring to FIG. 27, a plurality of reflective layers 135 may extend in the second direction (the Z-direction) and may be disposed and spaced apart in the first direction (the X-direction). An arrangement of a first recess 128 and a second recess 127 may be appropriately modified according to a position of an electrode pad and the like.

Referring to FIG. 28, a first recess 128 and a first electrode 142 may respectively extend in the first direction and the second direction. Thus, a plurality of second regions 137 may be formed in regions provided by intersection of the first recess 128 and the first electrode 142.

A plurality of reflective layers 135 may be disposed in the plurality of second regions 137 to reflect light upward. A lateral reflection part 135b may be disposed on an edge of a light emitting structure 120. The plurality of reflective layers 135 and the lateral reflection part 135b may be electrically connected to each other through a second electrode. However, the present invention is not limited thereto, and the plurality of reflective layers 135 and the lateral reflection part 135b may be electrically insulated from each other.

Figure 29:
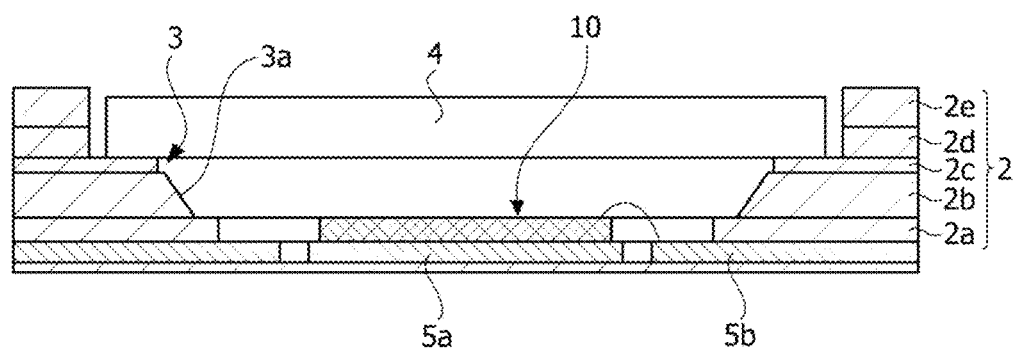
FIG. 29 is a conceptual view of a semiconductor device package according to one embodiment of the present invention.
Figure 30:
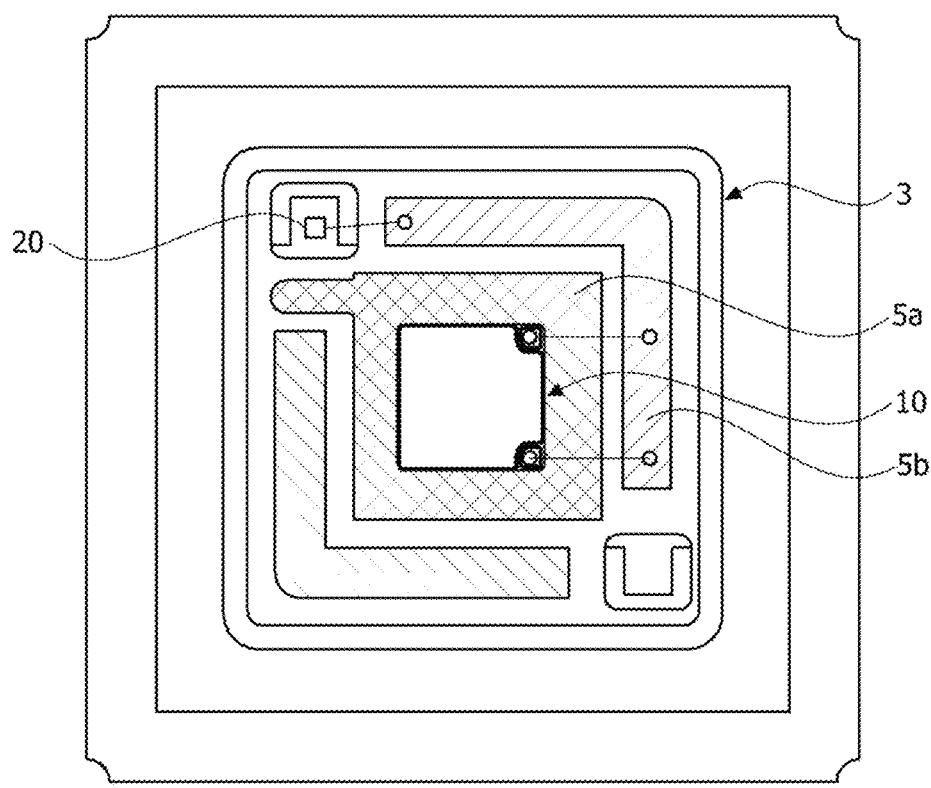
FIG. 30 is a plan view of the semiconductor device package according to one embodiment of the present invention.
Figure 31:
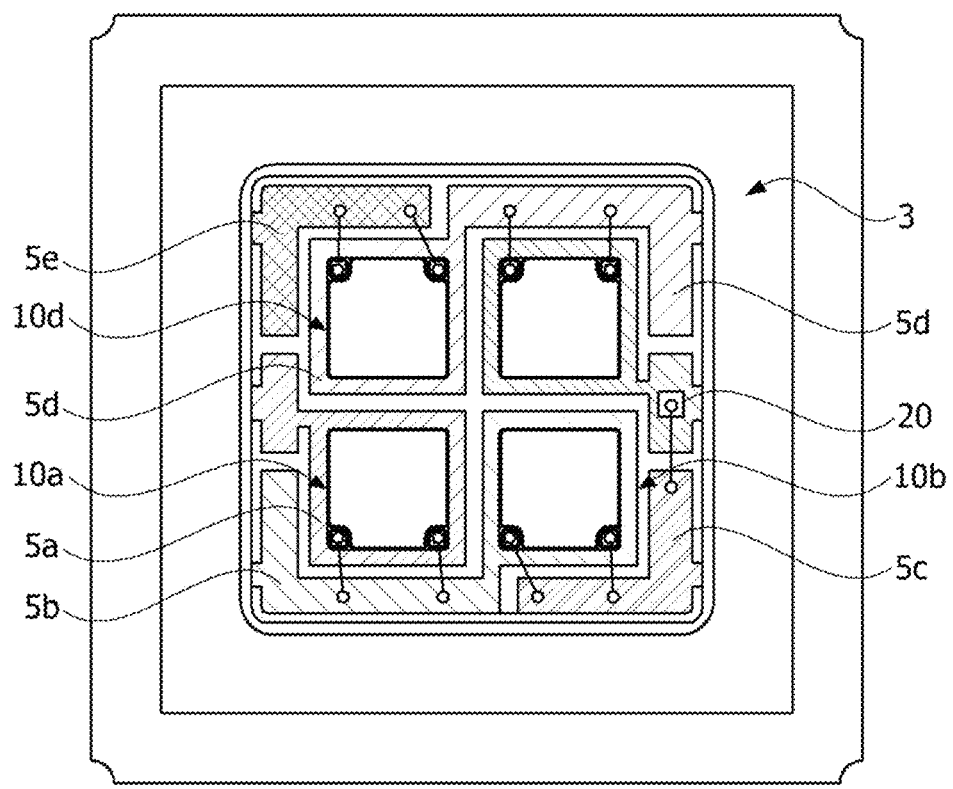
FIG. 31 is a modified embodiment of FIG. 30.

FIG. 29 is a conceptual view of a semiconductor device package according to one embodiment of the present invention, FIG. 30 is a plan view of the semiconductor device package according to one embodiment of the present invention, and FIG. 31 is a modified embodiment of FIG. 30.

Referring to FIG. 29, the semiconductor device package may include a body 2 having a recess 3 formed therein, a semiconductor device 1 disposed at the body 2, and a pair of lead frames 5a and 5b disposed at the body 2 and electrically connected to the semiconductor device 1. The semiconductor device 1 may include all the above-described configurations.

The body 2 may include a material or a coating layer which reflects UV light. The body 2 may be formed by stacking a plurality of layers 2a, 2b, 2c, 2d, and 2e. The plurality of layers 2a, 2b, 2c, 2d and 2e may be formed of the same material or different materials.

The recess 3 is formed to be wider as being away from the semiconductor device, and a stepped level 3a may be formed on an inclined surface.

A light transmitting layer 4 may cover the recess 3. The light transmitting layer 4 may be made of a glass material, but the present invention is not particularly limited thereto. A material of the light transmitting layer 4 is not particularly limited as long as the material can effectively allow light to transmit. An interior of the recess 3 may be an empty space.

Referring to FIG. 30, the semiconductor device 10 may be disposed on a first lead frame 5a and may be connected to a second lead frame 5b by a wire. In this case, the second lead frame 5b may be disposed to surround a lateral surface of the first lead frame.

Referring to FIG. 31, a plurality of semiconductor devices 10a, 10b, 10c, and 10d may be disposed at a semiconductor device package. In this case, a lead frame may include first to fifth lead frames 5a, 5b, 5c, 5d, and 5e.

A first semiconductor device 10a may be disposed on the first lead frame 5a and may be connected to the second lead frame 5b by wires. A second semiconductor device 10b may be disposed on the second lead frame 5b and may be connected to the third lead frame 5c by wires. A third semiconductor device 10c may be disposed on the third lead frame 5c and may be connected to the fourth lead frame 5d by wires. A fourth semiconductor device 10d may be disposed on the fourth lead frame 5d and may be connected to the fifth lead frame 5e by wires.

The semiconductor device may be applied to various types of light source devices. For example, a light source device may be a concept including a sterilization device, a curing device, a lighting device, a display device, a vehicular lamp, and the like. That is, the semiconductor device may be applied to various electronic devices disposed at a case and configured to provide light.

The sterilization device may include the semiconductor device according to the exemplary embodiments to sterilize a desired region. The sterilization device may be applied to household appliances such as a water purifier, an air conditioner, a refrigerator, and the like but is not limited thereto. That is, the sterilization device may be applied to various products requiring sterilization (e.g., medical equipment).

For example, the water purifier may include the sterilization device according to the exemplary embodiments to so as to sterilize circulating water. The sterilization device may be disposed at a nozzle or an outlet through which water circulates and may irradiate UV light. In this case, the sterilization device may include a waterproof structure.

The curing device may include the semiconductor device according to the exemplary embodiments to cure various kinds of liquids. The liquids may be a broadest concept including various materials which are cured upon exposure to UV light. For example, the curing device may cure various types of resins. Alternatively, the curing device may be applied to cure a cosmetic product such as a manicure.

The lighting device may include a light source module having a substrate and the semiconductor device of the exemplary embodiments, a heat dissipation part configured to dissipate heat of the light source module, and a power supplier configured to process or convert an electrical signal provided from the outside to provide the electrical signal to the light source module. Further, the lighting device may include a lamp, a headlamp, a street lamp, or the like.

The display device may include a bottom cover, a reflector, a light emitting module, a light guiding panel, an optical sheet, a display panel, an image signal output circuit, and a color filter. The bottom cover, the reflector, the light emitting module, the light guiding panel, and the optical sheet may constitute a backlight unit.

The reflector may be disposed on the bottom cover, and the light emitting module may emit light. The light guiding panel may be disposed ahead of the reflector to guide the light emitted from the light emitting module forward, and the optical sheet may include a prism sheet or the like and may be disposed ahead of the light guiding panel. The display panel may be disposed ahead of the optical sheet, the image signal output circuit may supply an image signal to the display panel, and the color filter may be disposed ahead of the display panel.

When the semiconductor is used as the backlight unit of the display device, the semiconductor device may be used as an edge type backlight unit or a direct-type backlight unit.

The semiconductor device may include a laser diode in addition to the above-described light emitting diode.

Like the light emitting device, the laser diode may include the first conductive semiconductor layer, the active layer, and the second conductive semiconductor layer of the above-described structure. Further, the laser diode uses an electro-luminescence phenomenon in which light is emitted when a current flows after a p-type first conductive semiconductor and an n-type second conductive semiconductor are bonded, but there are differences in directivity and phase of emitted light between the light emitting device and the laser diode. That is, the laser diode may emit light having the same phase in the same direction at a specific single wavelength (i.e., a monochromatic beam) using a phenomenon referred to as stimulated emission and a constructive interference phenomenon, and, with the above-described characteristic, the laser diode may be used for optical communication, medical equipment, semiconductor processing equipment, and the like.

An example of a light receiving device may include a photodetector which is a kind of transducer that detects light and converts an intensity of the detected light into an electric signal. As the photodetector, there is a photoelectric cell (silicon and selenium), an optical conversion device (cadmium sulfide and cadmium selenide), a photodiode (PD) (e.g., a PD having a peak wavelength in a visible blind spectral region or in a true blind spectral region), a phototransistor, a photomultiplier tube, a photoelectric tube (e.g., a vacuum and gas-filled type), an infra-red (IR) detector, and the like, but the embodiments is not limited thereto.

Further, the semiconductor device such as the photodetector may be manufactured using a direct bandgap semiconductor of which photoconversion efficiency is generally excellent. Alternatively, the photodetector has a variety of structures, and includes a pin-type photodetector using a p-n junction which is a most general structure, a Schottky-type photodetector using a Schottky junction, and a metal-semiconductor-metal (MSM)-type photodetector.

Like the light emitting device, the PD may include the first conductive semiconductor layer, the active layer, and the second conductive semiconductor layer of the above-described structure and may be formed of a p-n junction or a pin structure. The PD operates by applying a reverse bias or a zero bias, and, when light is incident into the PD, electrons and holes are generated and thus a current flows. At this point, an amount of the current may be approximately proportional to an intensity of the light incident into the PD.

A photovoltaic cell or a solar cell is one kind of the PD and may convert light into a current. Like the light emitting device, the solar cell may include the first conductive semiconductor layer, the active layer, and the second conductive semiconductor layer of the above-described structure.

Further, the solar cell may be used as a rectifier of an electronic circuit through a rectifying characteristic of a general diode using a p-n junction, and may be applied to an oscillation circuit and the like by being employed to a microwave circuit.

Further, the above-described semiconductor device is not necessarily implemented with a semiconductor, and in some cases, the semiconductor device may further include a metal material. For example, the semiconductor device such as the light-receiving device may be implemented using at least one among Ag, Al, Au, In, Ga, N, Zn, Se, P, and As or may also be implemented using a semiconductor material doped with a p-type or n-type dopant or an intrinsic semiconductor material.

While the present invention has been mainly described with reference to the exemplary embodiments, it should be understood that the present invention is not limited to the disclosed exemplary embodiments, and various modifications and applications can be devised by those skilled in the art to which the present invention pertains without departing from the gist of the present invention. For example, each component specifically shown in the exemplary embodiments can be modified and implemented. It should be construed that differences related to these modifications and applications will fall within the scope of the present invention defined by the appended claims.

The invention claimed is:

1. A semiconductor device comprising:
a semiconductor structure including a first conductive semiconductor layer, a second conductive semiconductor layer, an active layer disposed between the first conductive semiconductor layer and the second conductive semiconductor layer, a plurality of first recesses disposed up to a region of the first conductive semiconductor layer by passing through the second conductive semiconductor layer and the active layer, and a second recess disposed between the plurality of first recesses;
a plurality of first electrodes disposed inside the plurality of first recesses and electrically connected to the first conductive semiconductor layer;
a plurality of second electrodes electrically connected to the second conductive semiconductor layer; and
a reflective layer disposed inside the second recess,
wherein the semiconductor structure generates light in an ultraviolet wavelength range;
the sum of areas of the plurality of first recesses and an area of the second recess is in a range of 60% or less relative to a maximum area of the semiconductor structure in a first direction;

the areas of the plurality of first recesses and the area of the second recess are areas formed on a lower surface of the semiconductor structure, and the first direction is a direction perpendicular to a thickness direction of the semiconductor structure, and wherein the semiconductor device further comprises:

a lower reflective layer electrically connected to the plurality of first electrodes; and a substrate electrically connected to the lower reflective layer.

2. The semiconductor device of claim 1, wherein a distance between the plurality of second electrodes is in a range of 3 μm to 60 μm.

3. The semiconductor device of claim 1, wherein a width of the reflective layer is in a range of 3 μm to 30 μm.

4. The semiconductor device of claim 1, wherein the distance between the plurality of second electrodes is equal to the width of the reflective layer.

5. The semiconductor device of claim 1, wherein:

an area in which the plurality of first electrodes are electrically connected to the first conductive semiconductor layer is in a range of 6.0% to 11.0% relative to the maximum area of the semiconductor structure in the first direction.

6. The semiconductor device of claim 1, wherein an area in which the plurality of second electrodes are electrically connected to the second conductive semiconductor layer is in a range of 40% to 60% relative to the maximum area of the semiconductor structure in the first direction.

7. The semiconductor device of claim 1, wherein a ratio of the area in which the plurality of first electrodes are electrically connected to the first conductive semiconductor layer to the area in which the plurality of second electrodes are electrically connected to the second conductive semiconductor layer is in a range of 1:4 to 1:10.

8. The semiconductor device of claim 1, wherein the semiconductor structure includes a plurality of first regions separated by the second recess and the plurality of first electrodes are disposed in the plurality of first regions.

9. The semiconductor device of claim 8, wherein an area of the first region is 2.0 to 5.0 times an area of the first electrode.

10. The semiconductor device of claim 8, wherein areas of the plurality of first regions are 2.0 to 5.0 times the areas of the plurality of first recesses.

11. The semiconductor device of claim 1, wherein the reflective layer includes an extension part extending from the second recess and configured to be in contact with the second electrode.

12. The semiconductor device of claim 11, further comprising a capping layer configured to cover the reflective layer and the second electrode.

13. The semiconductor device of claim 12, further comprising a second electrode pad electrically connected to the capping layer.

14. The semiconductor device of claim 1, wherein the light emitting structure generates light in an ultraviolet wavelength range.

15. The semiconductor device of claim 1, wherein the first conductive semiconductor layer includes a first layer disposed adjacent to the active layer and a second layer disposed on the first layer; and the second layer has an aluminum (Al) composition that is higher than that of the first layer; and the first electrode is disposed on the first layer.

16. The semiconductor device of claim 1, wherein the plurality of the first recesses is separated in a second direction and each of the plurality of the first recesses is extended in a first direction perpendicular to the second direction, wherein the second recess is disposed between the plurality of the first recesses.

17. The semiconductor device of claim 16, wherein a width of the plurality of the first recesses is larger than a width of the second recess.

18. The semiconductor device of claim 1, wherein the second recess is extended along a side surface of the light emitting structure so that the second recess surrounds the plurality of the first recesses.

* * * * *